US006867037B1

(12) United States Patent
Murasugi et al.

(10) Patent No.: US 6,867,037 B1
(45) Date of Patent: Mar. 15, 2005

(54) HIGH LEVEL SECRETORY EXPRESSION SYSTEM OF INTACT MK FAMILY PROTEIN

(75) Inventors: Akira Murasugi, Tokyo (JP); Yukio Asami, Kanagawa (JP); Isao Kido, Kanagawa (JP); Hideshi Kumai, Kanagawa (JP)

(73) Assignee: Meiji Dairies Corp. (JP)

( * ) Notice: Subject to any disclaimer, the term of this patent is extended or adjusted under 35 U.S.C. 154(b) by 0 days.

(21) Appl. No.: 09/762,842
(22) PCT Filed: Aug. 10, 1999
(86) PCT No.: PCT/JP99/04332
§ 371 (c)(1),
(2), (4) Date: Apr. 30, 2001
(87) PCT Pub. No.: WO00/09718
PCT Pub. Date: Feb. 24, 2000

(30) Foreign Application Priority Data

Aug. 10, 1998 (JP) .......................................... 10/236621
Mar. 26, 1999 (JP) .......................................... 11/084583

(51) Int. Cl.[7] .............................................. C12N 15/00
(52) U.S. Cl. .................................................. 435/320.1
(58) Field of Search ..................................... 435/320.1

(56) References Cited

U.S. PATENT DOCUMENTS 5,324,639 A  6/1994 Brierley et al.

FOREIGN PATENT DOCUMENTS

WO     WO 92/13951   *  8/1992  ............ C12N/15/14

OTHER PUBLICATIONS

Kurjan, Janet and Ira Herskowitz (Oct. 1982) "Structure of a Yeast Pheromone Gene (MF α): A Putative α–Factor Precursor Contains Four Tandem Copies of Mature α–Factor" Cell 30:933–943.

Winther, Jakob R. and Poul Sorensen (Oct. 1991) "Propeptide of carboxypeptidase Y provides a chaperone–like functions as well as inhibition of the enzymatic activity" Proc. natl. Acad. Sci. USA 88:9330–9334.

Cramer, Jane Harris, Kristi Lea, Michael D. Schaber, Richard A. Kramer (Jan. 1987) "Signal Peptide Specificity in Posttranslational Processing of the Plant Protein Phaseolin in Saccharomyces cerevisiae" Molecular and Cellular Biology 7(1):121–128.

Clare, J.J., F.B. Rayment, S.P. Ballantine, K. Sreekrishna, M.A. Romanos (May 1991) "High–level Expression of Tetanus Toxin Fragment C in Pichia Pastoris Strains Containing Multiple Tandem Integrations of the Gene" Bio/Technology 9:455–460.

Hinnen, Albert, James B. Hicks, and Gerald R. Fink (Apr. 1978) "Transformation of yeast" proc. Natl. Acad. Sci. USA 75(4):1929–1933.

Cregg, James M., Thomas S. Vedvick, William C. Raschke (Aug. 1993) "Recent Advances in the Expression of Foreign Genes in Pichia pastoris" Bio/Technology 11:905–910.

(List continued on next page.)

Primary Examiner—James Ketter
Assistant Examiner—Konstantina Katcheves
(74) Attorney, Agent, or Firm—Saliwanchik, Lloyd & Saliwanchik

(57) ABSTRACT

Under the regulation of a methanol-inducible alcohol oxidase gene (AOX1) promoter and a transcription termination sequence originating from Pichia pastoris, Pichia yeast, which has been transformed with an expression vector containing an MK family protein gene ligated to an a1 factor signal sequence originating from Saccharomyces cerevisiae, is cultured and an intact MK family protein is thus expressed and secreted in a large amount into the culture supernatant.

14 Claims, 17 Drawing Sheets

```
<------- 5'AOX1-------><-- PHO1 signal sequence ---------------------
.......TTATTCGAAACG/ATG TTC TCT CCA ATT TTG TCC TTG GAA ATT ATT TTA GCT TTG GCT ACT TTG CAA TCT GTC TTC GCTvCGA GAA TTC CCC GGG ATC CTT AGA CAT
-- PHO1 signal sequence ------------>v<-- Multicloning site ----->< -3'AOX1-
```

OTHER PUBLICATIONS

Tomomura, Mineko, Kenji Kadomatsu, Shyuichiro Matsubara, Takashi Muramatsu (Jun. 1990) "A Retinoic Acid–responsive Gene, MK, Found in the Teratocarcinoma System" *The Journal of Biological Chemistry* 265(18):1076510770.

Kadomatsu, Kenji, Mineko Tomomura and Takashi Muramatsu (Mar. 30, 1988) "cDNA Cloning and Sequencing of a New Gene Intensely Expressed in Early Differentiation Stages of Embryonal Carcinoma Cells and In Mid–Gestation Period of Mouse Embryogenesis" *Biochemical and Biophysical Research Communications* 151(3):1312–1318.

Li, Yue–Sheng, Peter G. Milner, Anil K. Chauhan, Mark A. Watson, Ruth M. Hoffman, Charles M. Kodner, Jeffrey Milbrandt, Thomas F. Deuel (Dec. 1990) "Cloning and Expression of a Developmentally Regulated Protein That Induces Mitogenic and Neurite Outgrowth Activity" *Science* 250:1690–1694.

Becker, Daniel M. and Leonard Guarente (1991) "High–Efficiency Transformation of yeast by Electroporation" *Methods in Enzymology* 194:182–187.

Merenmies, Jussi and Heikki Rauvala (Oct. 1990) "Molecular Cloning of the 18–kDa Growth–associated Protein of Developing Brain" *The Journal of Biological Chemistry* 265(28):16721–16724.

Ito, Hisao, Yasuki Fukuda, Kousaku Murata, Akira Kimura (Jan. 1983) "Transformation of Intact Yeast Cells Treated with Alkali Cations" *Journal of Bacteriology* 153(1):163–168.

Yokota, Chika, Shuji Takahashi, Akira Eisaki et al. (1998) "Midkine Counteracts the Activin Signal in Mesoderm Induction and Promotes Neural Formation" *J. Biochem* 123(2):339–346.

Kojima, Soichi, Hisako Muramatsu, Hiroshi Amanuma, Takashi Muramatsu (Apr. 1995) "Midkine Enhances Fibrinolytic Activity of Bovine Endothelial Cells" *The Journal of Biological Chemistry* 270(16):9590–9596.

Iwasaki, Wakana, Koji Nagata, Kideki Hatanaka et al. (1997) "Solution structure of midkine, a new heparin–binding growth factor" *The EMBO Journal* 16(23):6936–6946.

Kadomatsu, K., M. Hagihara, S. Akhter,Q–W Fan, H. Muramatsu and T. Muramatsu (1997) "Midkine induces the transformation of NIH3T3 Cells" *British Journal of Cancer* 75(3):354–359.

Wiren, Kristine M., John T. Potts, Jr., and Henry M. Kronenberg (Dec. 1988) "Importance of the Propeptide Sequence of Human Preproparathyroid Hormone for Signal Sequence Function" *The Journal of Biological Chemistry* 263(36):19771–19777.

Muramatsu, Hisako, Hiroshi Hamada, Shigetsugu Noguchi, Yuko Kamada and Takashi Muramatsu (1985) "Cell–surface Changes During in Vitro Differentiation of Pluripotent Embryonal Carcinoma Cells" *Developmental Biology* 110:284–296.

Weissman, Jonathan S. and Peter S. Kim (Nov. 1992) "The Pro Region of BPTI Facilitates Folding" *Cell* 71:841–851.

Chen, Yee–Hsiung, Jen Tsi Yang, Hugo M. Martinez (1972) "Determination of the Secondary Structures of Proteins by Circular Dichroism and Optical Rotatory Dispersion" *Biochemistry* 11(22):4120–4131.

Brankamp, R., et al., "Expression of a Synthetic Gene Encoding the Anticoagulant–Antimetastatic Protein Ghilanten by the Methylotropic Yeast *Pichia pastoris*", *Protein Expression and Purification*, 1995, pp. 813–820, vol. 6, Academic Press, Inc.

Murasugi, A. and Tohma–Aiba, Y., "Characterization of Partially Truncated Human Midkine Expressed in *Pichia pastoris*", *Biosci. Biotechnol. Biochem.*, Jun. 2002, pp. 1295–1300, vol. 66, No. 6.

Murasugi, A. and Tohma–Aiba, Y., "Comparison of Three Signals for Secretory Expression of Recombinant Human Midkine in *Pichia pastoris*", *Biosci. Biotechnol. Biochem.*, Oct. 2001, pp. 2291–2293, vol. 65, No. 10.

Rosenfeld, S., et al., "Production and Purification of Recombinat Hirudin Expressed in the Methylotrophic Yeast *Pichia pastoris*", *Protein Expression and Purification*, Dec. 1996, pp. 476–482, vol. 8, No. 4, Academic Press, Inc.

Sreekrishna, K., et al., "Strategies for Optimal Synthesis and Secretion of Heterologous Proteins in the Methylotrophic Yeast *Pichia pastoris*", *Gene*, Apr. 29, 1997, pp. 55–62, vol. 190, No. 1, Elsevier Science B.V..

Uehara, K., et al., "Genomic Structure of Human Midkine (MK), a Retinoic Acid–Responsive Growth/Differentiation Factor", *J Biochem*, May 1992; pp. 563–567, vol. 111, No. 5.

Milner, Peter G., Shah, Dulari, Veile, Rosalie, Donis–Keller, Helen and Kumar, Vijaya (1992) "Cloning, Nucleotide Sequence, and Chromosome Localization of the Human Pleiotrophin Gene" *Biochemistry* 31(48):12023–12028.

Database Geneseq Accession No. AAT12736, 1994.

* cited by examiner

Figure 1

<----- 5'AOX1 ------><-- PHO1 signal sequence -----------------
.......TTATTCGAAACG/ATG TTC TCT CCA ATT TTG TCC TTG GAA ATT ATT TTA GCT
TTG GCT ACT TTG CAA TCT GTC TTC GCTvCGA GAA TTC CCC GGG ATC CTT AGA CAT
-- PHO1 signal sequence ------------><-- Multicloning site -----><-3'AOX1-

Figure 3

......5'AOX1..TTCGAAGGATCCAAACG ATG AGA TTT CCT TCA ATT TTT ACT GCA GTT
                                Met Arg Phe Pro Ser Ile Phe Thr Ala Val
                                (1)

TTA TTC GCA GCA TCC TCC GCA TTA GCT|GCT CCA GTC AAC ACT ACA GAA GAT GAA
Leu Phe Ala Ala Ser Ser Ala Leu Ala▼Ala Pro Val Arg Ile Thr Thr Glu Asp Glu

ACG GCA CAA ATT CCG GCT GAA GCT GTC ATC GGT TAC TCA GAT TTA GAA GGG GAT TTC
Thr Ala Gln Ile Pro Ala Glu Ala Val Ile Gly Tyr Ser Asp Leu Glu Gly Asp Phe

GAT GTT GCT GTT TTG CCA TTT TCC AAC AGC ACA AAT AAC GGG TTA TTG TTT ATA AAT
Asp Val Ala Val Leu Pro Phe Ser Asn Ser Thr Asn Asn Gly Leu Leu Phe Ile Asn
                                                           Xho I           (2)
ACT ACT ATT GCC AGC ATT GCT GCT AAA GAA GAA GGG GTA TCT CTC GAG AAA AGA|GAG
Thr Thr Ile Ala Ser Ile Ala Ala Lys Glu Glu Gly Val Ser Leu Glu Lys Arg▼Glu (3) Hind III
    ┌Sna BI    Eco RI   Avr II   Not I
GCT|GAA GCT|TAC GTA    GAA TTC   CCT AGG   GCG GCC GCG ...
Ala▼Glu Ala▼Tyr Val    Glu Phe   Pro Arg   Ala Ala Ala

SEQUENCE LISTING

```
<160> NUMBER OF SEQ ID NOS: 12

<210> SEQ ID NO 1
<211> LENGTH: 562
<212> TYPE: DNA
<213> ORGANISM: Homo sapiens

<400> SEQUENCE: 1
atgcagcacc gaggcttcct cctcctcacc ctcctcgccc tgctggcgct cacctccgcg      60
gtcgccaaaa agaaagataa ggtgaagaag ggcggcccgg ggagcgagtg cgctgagtgg     120
gcctgggggc cctgcacccc cagcagcaag gattgcggcg tgggtttccg cgagggcacc     180
tgcgggcgcc agacccagcg catccggtgc agggtgccct gcaactggaa gaaggagttt     240
ggagccgact gcaagtacaa gtttgagaac tggggtgcgt gtgatggggg cacaggcacc     300
aaagtccgcc aaggcaccct gaagaaggcg cgctacaatg ctcagtgcca ggagaccatc     360
cgcgtcacca agccctgcac ccccaagacc aaagcaaagg ccaaagccaa gaaagggaag     420
ggaaaggact agacgccaag cctggatgcc aaggagcccc tggtgtcaca tggggcctgg     480
cccacgccct ccctctccca ggcccgagat gtgaccacc agtgccttct gtctgctcgt      540
tagctttaat caatcatgcc cc                                               562

<210> SEQ ID NO 2
<211> LENGTH: 143
<212> TYPE: PRT
<213> ORGANISM: Homo sapiens

<400> SEQUENCE: 2

Met Gln His Arg Gly Phe Leu Leu Leu Thr Leu Leu Ala Leu Leu Ala
1               5                   10                  15

Leu Thr Ser Ala Val Ala Lys Lys Lys Asp Lys Val Lys Lys Gly Gly
```

-continued

```
                20                  25                  30
Pro Gly Ser Glu Cys Ala Glu Trp Ala Trp Gly Pro Cys Thr Pro Ser
            35                  40                  45

Ser Lys Asp Cys Gly Val Gly Phe Arg Glu Gly Thr Cys Gly Ala Gln
 50                  55                  60

Thr Gln Arg Ile Arg Cys Arg Val Pro Cys Asn Trp Lys Lys Glu Phe
 65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
            115                 120                 125

Lys Thr Lys Ala Lys Ala Lys Lys Gly Lys Gly Lys Asp
        130                 135                 140
```

<210> SEQ ID NO 3
<211> LENGTH: 48
<212> TYPE: DNA
<213> ORGANISM: Homo sapiens

<400> SEQUENCE: 3
gcgcccgaat tcaaaaagaa agataaggtg aagaagggcg gcccgggg        48

<210> SEQ ID NO 4
<211> LENGTH: 46
<212> TYPE: DNA
<213> ORGANISM: Homo sapiens

<400> SEQUENCE: 4
gcgcccgaat tcttagtcct ttcccttccc tttcttggct ttggcc          46

<210> SEQ ID NO 5
<211> LENGTH: 60
<212> TYPE: DNA
<213> ORGANISM: Homo sapiens

<400> SEQUENCE: 5
gcgcccctcg agaaaagaga ggctgaagct aaaaagaaag ataaggtgaa gaaggggcggc  60

<210> SEQ ID NO 6
<211> LENGTH: 507
<212> TYPE: DNA
<213> ORGANISM: Homo sapiens

<400> SEQUENCE: 6
atgcaggctc aacagtacca gcagcagcgt cgaaaatttg cagctgcctt cttggcattc      60
attttcatac tggcagctgt ggatactgct gaagcaggga gaaagagaa accagaaaaa     120 aaagtgaaga agtctgactg tgagaatggc agtggagtg tgtgtgtgcc caccagtgga     180
gactgtgggc tgggcacacg ggagggcact cggactggag ctgagtgcaa gcaaaccatg    240
aagacccaga gatgtaagat ccctgcaac tggaagaagc aatttggcgc ggagtgcaaa    300
taccagttcc aggcctgggg agaatgtgac ctgaacacag ccctgaagac agaactgga    360 agtctgaagc gagccctgca caatgccgaa tgccagaaga ctgtcaccat ctccaagccc    420
tgtggcaaac tgaccaagcc caaacctcaa gcagaatcta agaagaagaa aaggaaggc    480 aagaaacagg agaagatgct ggattaa                                       507

```
<210> SEQ ID NO 7
<211> LENGTH: 168
<212> TYPE: PRT
<213> ORGANISM: Homo sapiens

<400> SEQUENCE: 7

Met Gln Ala Gln Gln Tyr Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Ser Asp Cys Gly
            35                  40                  45

Glu Trp Gln Trp Ser Val Cys Val Pro Thr Ser Gly Asp Cys Gly Leu
50                      55                      60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 8
<211> LENGTH: 48
<212> TYPE: DNA
<213> ORGANISM: Homo sapiens

<400> SEQUENCE: 8
gcgcccctcg agaaaagagg gaagaaagag aaaccagaaa aaaaagtg                 48

<210> SEQ ID NO 9
<211> LENGTH: 42
<212> TYPE: DNA
<213> ORGANISM: Homo sapiens

<400> SEQUENCE: 9
gcgcccgaat tcttaatcca gcatcttctc ctgtttcttg cc                       42

<210> SEQ ID NO 10
<211> LENGTH: 5
<212> TYPE: PRT
<213> ORGANISM: Homo sapiens

<400> SEQUENCE: 10

Tyr Val Glu Phe Lys
1               5

<210> SEQ ID NO 11
<211> LENGTH: 7
<212> TYPE: PRT
<213> ORGANISM: Homo sapiens

<400> SEQUENCE: 11
```

```
Tyr Val Glu Phe Lys Lys Lys
1               5

<210> SEQ ID NO 12
<211> LENGTH: 12
<212> TYPE: PRT
<213> ORGANISM: Homo sapiens

<400> SEQUENCE: 12

Tyr Val Glu Phe Lys Lys Lys Asp Lys Val Lys Lys
1               5                   10
```

HIGH LEVEL SECRETORY EXPRESSION SYSTEM OF INTACT MK FAMILY PROTEIN

TECHNICAL FIELD

The present invention relates to a high level secretory expression system of an intact MK family protein by recombinant DNA techniques using methylotrophic yeast as the host.

BACKGROUND ART

MK is a growth factor discovered as the retinoic acid responsive gene product, and is a polypeptide that is rich in basic amino acids and cysteine and that has the molecular weight 13 kDa (Kadomatsu, K. et al.: Biochem. Biophys. Res. Commun., 151: 1312–1318, 1988; Tomomura, M. et al.: J. Biol. Chem., 265: 10765–10770, 1990). MK has 45% sequence homology to another heparin-binding protein referred to as pleiotrophin (PTN) or heparin-binding growth associated molecule (HB-GAM).

MK and PTN have common activities such as the neurotrophic factor activity (Li, Y.-S. et al.: Science, 250: 1690–1694, 1990; Merenmies, J. & Rauvala, H.: J. Biol. Chem., 265: 16721–16924, 1990; Muramatus, H. et al.: Dev. Biol., 110: 284–296, 1985), the enhancement of fibrinolytic system (Kojima, S. et al.: J. Biol. Chem., 270: 9590–9596, 1995), proliferation of various cells, transformation of NIH3T3 cells (Kadomatsu, K. et al.: Brit. J. Cancer, 75: 354–359, 1997; Yokota, C. et al.: J. Biochem., 123, 339–346, 1998), and angiogenesis.

Thus, these MK family proteins are expected to be useful as drugs, and the development of high level expression system of these proteins has been strongly demanded. Natural MK and PTN proteins are not glycosylated. Therefore, the high level expression of these proteins with no glycosylation by recombinant DNA techniques, would be extremely useful not only for production of the proteins as drugs but also for structural and functional analyses of the proteins. In this invention, an unglycosylated MK family protein is referred to as an intact MK family protein. Herein, an MK family protein means a protein comprising at least the amino acid sequence of a mature protein of MK, PTN, or their functionally equivalent mutants. In addition, unglycosylated MK and PV are herein referred to as intact MK and intact PTN, respectively.

As the expression system for an MK family protein, the methanol-metabolizing yeast (referred to as "methylotrophic yeast" hereafter) is thought to be appropriate. In general, from the viewpoint that yeast in a unicellular eucaryote, abundant in molecular biological information, safe for humans, and easily cultured, it has been used as the host cell in the production of useful proteins by recombinant DNA techniques. In the secretory expression system of yeast, in particular, since the expressed protein in released to the outside of cells, the continuous culturing can be carried out with the expectation of a great deal increase in the production. Furthermore, since the labor to disrupt cells is saved, protein purification becomes easy.

In view of these facts, the present inventors have attempted to establish a high level secretory expression system of MK proteins using methylotrophic yeast, *Pichia pastoris*, as the host. An expression system of foreign genes by Pichia pastoris has been developed and reported in the production of hepatitis type B vaccine and a high-level secretory expression of invertase (Cregg, J. M. et al.: Bio/Technology, 11: 905–910, 1993). However, in the case where the secretion signal unique to MK protein is used for its expression, the expression level thereof is low (30–50 mg/L), and, furthermore, a majority of MK proteins thus expressed are bound to sugars originating in yeast which are different from those attached in animal cells. That is, the content of intact MK protein is extremely low. Use of MK proteins having sugars derived from yeast as drugs poses problems of antigenicity. Therefore, it becomes necessary to isolate and purify intact MK protein from expression products. However, it is highly difficult to isolate and purify proteins that have a common amino acid sequence but differ only in the attached sugars.

To increase an expression level of intact MK protein, the present inventors produced a large number of expression host strains in which the copy number of the expression cassette was increased, and allowed them to express the protein. They obtained yeast strains that produce an about 2-fold higher expression level than that obtained in conventional strains in the fermentor culture. However, they failed to acquire strains that highly express intact MK protein, indicating that an increase in the copy number is not directly related to the expression of MK protein.

DISCLOSURE OF THE INVENTION

An object of the present invention is to establish a high level secretory expression system of an intact MK family protein using methylotrophic yeast as a host.

To solve the above-described problems, the present inventors have actively studied and, as a result, constructed an expression vector for an MK family protein by ligating cDNA encoding a mature MK family protein immediately downstream of the prepro-sequence of α1 factor gene of *Saccharomyces cerevisiae* under the regulation of an alcohol oxidase promoter of methylotrophic yeast, transformed methylotrophic yeast using the vector, and found that the transformant thus obtained expressed a large amount of the active form of an intact MK family protein and secreted it into the culture medium. Furthermore, the present inventors have elucidated that a combination of the signal sequence of α1 factor with a gene encoding a mature MK family protein is important for the expression of an intact MK family protein, completing this invention.

Specifically, the present invention relates to the following vectors and method for producing an intact MK family protein, the method comprising culturing transformants transformed with these vectors and recovering an intact MK family protein as a secretory expression product.

(1) A vector for secretory expression of an intact MK family protein in methylotrophic yeast, said vector comprising a gene encoding a mature MK family protein ligated to a signal sequence of α1 factor derived from *Saccharomyces cerevisiae*.

(2) The vector according to (1) comprising components (a) to (g) below:
 (a) a promoter sequence of a methanol-inducible alcohol oxidase gene (AOX1) derived from *Pichia pastoris*,
 (b) a signal sequence of α1 factor derived from *Saccharomyces cerevisiae*,
 (c) a gene encoding a mature MK family protein, wherein said gene is ligated to (b),
 (d) a transcription termination sequence of a methanol-inducible alcohol oxidase gene (AOX1) derived from *Pichia pastoris*,
 (e) a selection marker gene functioning in *Escherichia coli* and methylotrophic yeast, (f) a replication origin functioning in *Escherichia coli*, and (g) 5' AOX1 and 3' AOX1 for the site-specific homologous recombination to a methylotrophic yeast chromosomal DNA.

(3) The vector according to (1), wherein said MK family protein is MK protein.

(4) The vector according to (1), wherein said MK family protein is PTN protein.

(5) A transformant comprising methylotrophic yeast transformed with the vector according to any one of (1) to (4).

(6) The transformant according to (5), wherein said transformant is pPIC9DP-hMK/SMD1168, said vector is the one according to (3), and said methylotrophic yeast is strain SMD1166.

(7) The transformant according to (5), wherein said transformant is pPIC9-hPTN/GS115, said vector is the one according to (4), and said methylotrophic yeast is strain GS115.

(8) A method for producing an intact MK family protein, said method comprising culturing the transformant according to any one of (5) to (7) and recovering secretory expression products.

(9) The method according to (8), said method comprising:
(a) culturing the transformant according to (6),
(b) inducing the expression of MK protein under the conditions of 20° C. and pH 3 after the proliferation at pH 4, and
(c) recovering secretory expression products.

In general, a secretory protein is synthesized as a precursor having at its N-terminal side a sequence comprising 20 to 30 amino acids referred to as a signal sequence (presequence). Furthermore, besides this signal sequence, most of hydrolases such as proteases, hormones, growth factors, etc. have an additional portion referred to as a pro-sequence, which is adjacent to the mature portion. The reported analytical results on the function of this pro-sequence include that it is essential for the correct formation of disulfide bonds of the mature protein (Weissman, J. S. & Kim, P. S.: Cell, 71: 841–851, 1992), that it is involved in membrane permeability of the mature protein (Wiren, K. M. et al.: J. Biol. Chem., 263: 19771–19777, 1988), and that it interacts with the mature protein to stimulate the formation of active correct conformation thereof (Winther, J. L. & Sorensen, P.: Proc. Natl. Acad. Sci. USA., 88: 9330–9334, 1991). However, other functions still remain to be elucidated. It has been reported that replacing the signal sequence with other signal sequence or prepro-sequence remarkably decreases the efficiency of the removal of signal peptide and glycosylation (Cramer, J. H. et al.: Mol. Cell Biol., 7: 121, 1987). Herein, the prepro-sequence is also referred to as "signal sequencer". The "signal sequence" refers to not only an amino acid sequence but also a nucleotide sequence of a cDNA encoding the amino acid sequence.

Among secretory proteins or yeast, signal sequence structures of genes have been elucidated for invertase (SUC2), acidic phosphatase (PHO5 and PHO3), α-galactosidase (MEL1), α-factor (MFα1 and MFα2), a-factor (MFa1 and MFa2), double-stranded RNA killer toxin (KILM1), killer toxin of linear DNA plasmid (KIL97 and KIL28), etc. MF+1, MFα2, KILM1, and KIL97 have prepro-structures. Signal sequence of MFα1, which is most frequently used in secretory production of foreign proteins, comprises 85 to 89 amino acid residues (J. Kurjian & I. Herskowitz: Cell, 36: 933, 1982).

An expression vector used to markedly elevate secretory production of a foreign protein, fundamentally comprises cDNA encoding the protein region or a gene containing no intron immediately downstream of the secretion signal, which is inserted between a promoter and terminator functioning in yeast. A signal carried by the gene for a secretory protein unique to yeast or a secretion signal derived from other than yeast is used as the secretion signal.

Expression vectors used for secretory production of an MK family protein of this invention can be constructed by the standard method described in "J. Sambrook, E. F. Fritsch, and T. Maniatis; Molecular Cloning: A Laboratory Manual, Second Edition, Cold Spring Harbor Laboratory Press, Cold Spring Harbor, N.Y., USA, 1989". An expression vector of appropriate methylotrophic yeast can be used. Vectors suitable for implementing this invention are those functioning in preferably the genus *Pichia* and most preferably *Pichia pastoris* GS115 (accession number: NRRL Y-15851). For example, the expression vector pPIC9 (Phillips Petroleum Co.) shown in FIG. 5 is used as one of the preferred expression vectors in this invention. The vector is a shuttle vector carrying, as the selection marker, genes required for selection in *Escherichia coli* and *Pichia pastoris*, namely, ampicillin resistance gene and *Pichia histidinol* dehydrogenase gene (HIS4). In addition, this expression vector comprises the following elements:

replication origin functioning in *Escherichia coli* (Co1E1), promoter of *Pichia* alcohol oxidase for expression of a foreign gene (5' AOX1), DNA encoding *Saccharomyces cerevisiae* α1factor secretion signal (s), transcription termination sequence of AOX1 gene (3' AOX1-TT), and 3' AOX1 involved, together with 5' AOX1, in the site-specific integration into *Pichia pastoris* chromosomal DNA.

The two insertion site in anal-factor signal sequence for foreign gene have been reported: (1) at the C-terminal side of Lys 85 and (2) at the C-terminal side of Ala 89 (Fumio Hishinuma: Kagaku To Seibutsu, 26: 568–576, 1988). This invention is characterized in that, an α1-factor signal sequence of *Saccharomyces cerevisiae* as shown in FIG. 3 is used in place of the signal sequence of an MK family protein itself. It is preferable to insert the gene encoding a mature MK protein immediately downstream of the spacer sequence (Glu-Ala-Glu-Ala) following the final Lys-Arg sequence of the prepro-sequence of α1-factor (i.e. the insertion site (2) described above) or at the EcoRI site located downstream of it. The gene encoding a mature PTN protein is preferably inserted immediately downstream of the final Lys-Arg sequence.

The structural genes for MK family proteins are known. The human MK gene encodes a signal peptide with 22 amino acids stretching from Met (ATG at 1 to 3) to Ala (GCC at 67 to 69) followed by a mature protein with 121 amino acids from Lys (AAA at 67 to 69) to Asp (GAC at 427 to 429) (cf. the nucleic acid sequence of SEQ ID NO: 1 and the amino acid sequence of SEQ ID NO: 2). The gene for PTN protein encodes a signal peptide with 32 amino acids from Met (ATG at 1 to 3) to Ala (GCA at 94 to 96) followed by a mature protein with 136 amino acids from Gly (AAA at 97 to 99) to Asp (GAT at 502 to 504) of the nucleic acid sequence of SEQ ID NO: 6 and the amino acid sequence of SEQ ID NO: 7). MK family proteins of the present invention include not only proteins comprising the amino acid sequence identical to the natural amino acid sequence but also mutants having the activity functionally equivalent to MK protein and comprising the amino acid sequence in which one or more amino acids are substituted, deleted, added, and/or inserted. Furthermore, intact MK protein of this invention means a protein that comprises at least the amino acid sequence of a mature protein of MK protein, which is not glycosylated. Activity of an MK family protein can be evaluated, as described in examples, for example, by the cell proliferation-promoting activity for the fibroblast strain NIH3T3 derived from a fetal Swiss mouse. In addition, those skilled in the art can modify the M or F gene sequences without damaging biological functions of the corresponding protein.

A gene encoding an MK family protein can be amplified by PCR using a set of sense and antisense PCR primers suitable for amplification of the gene (in the case of MK gene, SEQ ID NOs: 3 or 5 and 4, and in the case of PTN gene, SEQ ID NOs: 8 and 9) with the gene of the protein as a template. In this case, primers are designed so as to include the appropriate restriction enzyme recognition site which is contained in the expression vector. Then, the gene is inserted into the appropriate restriction enzyme cleavage site of an expression vector. *Escherichia coli* strain HB101 or XL1-Blue MRF' is transformed with the expression vector containing the gene of a mature MK family protein. Several transformed *Escherichia coli* clones are selected, and PCR is performed with the expression vector contained in these clones as the template using appropriate primers to confirm that the inserted gene is in the correct orientation. The nucleotide sequences of the MK gene and region near the insertion site of this expression vector are determined to confirm no error in the sequence.

Yeasts used as a host include any of appropriate methylotrophic yeasts. The methylotrophic yeast includes strains capable of proliferation in the presence of methanol, such as those belonging to genera *Hansenula, Candida, Kloeckera, Pichia, Saccharomyces*, and *Rhodotorula*. Methylotrophic yeast belonging to genus *Pichia* such as an auxotrophic *Pichia pastoris* strain GS115 (NRRL Y-15851), etc. is preferable. When methylotrophic yeast with its protease activity reduced such as SMD1168 (Phillips Petroleum Company) is used as the host, the decomposition of expression product by protease can be suppressed. Known methods such as protoplast method (Hinen, A. et al.: Proc. Natl. Acad. Sci. USA, 75: 1929, 1978), lithium method (Ito, H. et al.: J. Bacteriol., 153: 163, 1983), or electroporation method [D. M. Becker and L. Guarente, "Method in Enzymology" ed. by C. Gutherie, G. Fink, Vol. 194, p. 182, Academic Press, New York (1991)], and the like can be used as the transformation method for transferring the expression vector containing the gene encoding an MK family protein. For example, when electroporation method is used, the protocol of Invitrogen (e.g., pPICZAα, B, C, Version A, 160410, 25-0150) can be employed.

Methylotrophic yeast thus transformed can be isolated by selecting auxotrophic yeast in growth medium containing no nutrient (depending on the auxotrophy of the yeast) and then those with a novel phenotype ("capability to utilize methanol +/−, Mut +/−"). When the transformant contains a drug resistance gene, the transformant can be selected by culturing in the presence of antibiotic that is toxic to yeast. However, isolation methods are not limited to them.

Transformed methylotrophic yeast thus isolated is cultured by suitable culturing techniques such as shaking culture in a flask, high density culture, etc. An MK family protein is expressed by the method suitable for the expression regulation region contained in the vector. For example, in pPIC9, in which the promoter of alcohol oxidase is the expression regulation region, the expression of a gene under the regulation of the promoter can be induced by culturing transformed yeast in the presence of in ethanol (cf. Unexamined Published Japanese Patent Application (JP-A)Nos. Hei 7-11189 and Hei 8-228779).

FIG. 6 compares by ELISA expression levels of MK protein in the fermentor cultures of the expression strain using the signal sequence of human MK protein (pHILD4-hMK/GS115) and the expression strain containing the signal sequence of α1 factor (pPIC9K-4AhMK/GS115). In the case of the expression strain containing the signal sequence of human MK protein, the expression level is 30 to 50 mg/L in the 4-day culture, while, in the case of the expression strain containing the signal sequence of α1 factor, the expression level is about 200 mg/L, which rises to about 240 mg/L by addition of EDTA to the culture medium. On the other hand, in the assay of the same sample by FPLC analysis, as shown in FIG. 7, the expression level obtained by addition of EDTA is about 640 mg/L (MK protein 1 mg/mL=1.8 $A_{240}$) clearly demonstrating that expression level can be increased 5-fold or more by using the signal sequence of α1 factor than the case of using the signal sequence of human MK itself. After the expression strain utilizing the signal sequence of MK itself (pHILD4-hMK/GS115) is cultured, MK thus expressed is purified with SP Sepharose and heparin Sepharose and subjected to mass spectrometry by MALDI method (matrix-assisted laser desorption ionization/time-of-flight mass spectrometer). The results are shown in FIG. 11. Although the peak for intact MK is highest (13241.6), peaks of MK presumably associated with 1 to 18 sugar molecules are observed, and the total amount of these peaks greatly surpass the expression level of intact MK.

Mass spectrometry of MK protein purified from the supernatant of fermentor culture of the expression strain pPIC9K-4AhMK/GS115 showed, besides intact MK protein, proteins with deletions of 5 amino acids Tyr-val-Glu-Phe-Lys, 7 amino acids Tyr-Val-Glu-Phe-Lys-Lys-Lys, and 12 amino acids Tyr-Val-Glu-Phe-Lys-Lys-Lys-Asp-Lys-Val-Lys-Lys, from the amino terminus, as shown in FIG. 8. In addition, amino terminal analysis of expression products detected Tyr, Lys, and Asp, and these residues match amino acids at the amino termini of proteins resulted from deletion of five and seven amino acids from the amino terminus of the expected expression product MK protein. However, no clear signal for glycosylated MK is observed. These results clearly indicate association of few sugars with MK.

It is evident that use of the signal sequence of α1 factor remarkably elevates the expression level of intact MK protein and reduces glycosylation of an MK family protein as compared with the case of using the signal sequence of MK itself.

Furthermore, FPLC measurement of the expression level of MK protein in the fermentor culture of the expression strain pPIC9DP-hMK/SMD1168 shows that, as represented in FIG. 9, the expression level reaches the maximum (360 mg/L) on the eighth day of culture. Mass spectrometry of MK protein purified from 10 ml of the culture solution on the seventh day gives, as shown in FIG. 10, a value 13241.2 (+1), approximately the same as the value 13241.3 (+1), the theoretical molecular weight of MK protein, showing no signal due to the glycosylated MK. When using SMD1168 in place of G5115 as the host and altering culture conditions, the amount of degradation products has become extremely small. As shown in Table 1, the amino acid sequence at the amino terminus of the expression product coincides with that of intact MK protein. The result of amino acid composition analysis also matches well the expected values and values found for the chemically synthesized mature HE protein (standard substance) as shown in Table 2.

When the thus-obtained intact MK protein of this invention is examined for its biological activity based on the cell proliferation-promoting activity for NIH3T3 cells, a dose-dependent increase in the number of viable cells is observed as shown in FIG. 13.

Results of circular dichroism (CD) spectrum measured to obtain the secondary structure of the intact MK protein obtained by this invention are shown in FIG. 12. Overall pattern of the spectrum resembles a spectrum of protein comprising antiparallel β-structures. A shoulder presumably derived from a negative peak near 215 nm is clearly observed, which is thought to indicate β-structures. The results of CD spectrum is well consistent with the reported results of NMR analysis for MK protein showing that almost nothing but β-structure (Iwasaki, W. et al.: EMBO J. 16: 6936–6946, 1997). These results indicate that the intact MK protein obtained by this invention well retains the tertiary structure of MK protein. In addition, in this invention, intact PTN protein can also be obtained in such a high yield as 250 mg/L as shown by the HPLC elution profile in FIG. 14 and by the results of mass spectrometry in FIG. 16. Thus, this invention also provides a high level secretory expression system for intact PTN protein.

BRIEF DESCRIPTION OF THE DRAWINGS

FIG. 1 shows the nucleotide sequence of secretion signal portion of *Pichia* yeast acidic phosphatase. Symbol v represents the cleavage site of the corresponding signal peptide.

FIG. 3 represents the nucleotide sequence of α1 factor secretion signal portion originating from *Saccharomyces cerevisiae*. "(1)" represents the cleavage site of pre-sequence, "(2)", that of prepro-sequence, and "(3)", that of dipeptidylaminopeptidase.

BEST MODE FOR CARRYING OUT THE INVENTION

In the following, the present invention is more specifically described with reference to examples, but is not construed as being limited thereto.

EXAMPLE 1

Construction of Expression Vector for MK Protein

Three kinds of expression vectors for human MK protein containing secretion signal sequences were constructed.

Construction of the expression vectors was carried out according to the standard method as described, for example, by J. Sambrook, E. F. Fritsch and T. Maniatis (Molecular cloning: A Laboratory Manual, Second Edition (1989), Cold spring Harbor Laboratory Press, Cold Spring Harbor, N.Y., USA).

(1) Expression vector comprising the secretion signal sequence unique to MK protein The MK protein expression vector "pHILD4-hMK" according to Example 1 of JP-A Hei 9-95454 was used as the expression vector comprising the secretion signal sequence unique to MK protein.

(2) Construction of expression vector comprising the secretion signal sequence of PHO1.

Figure 2:
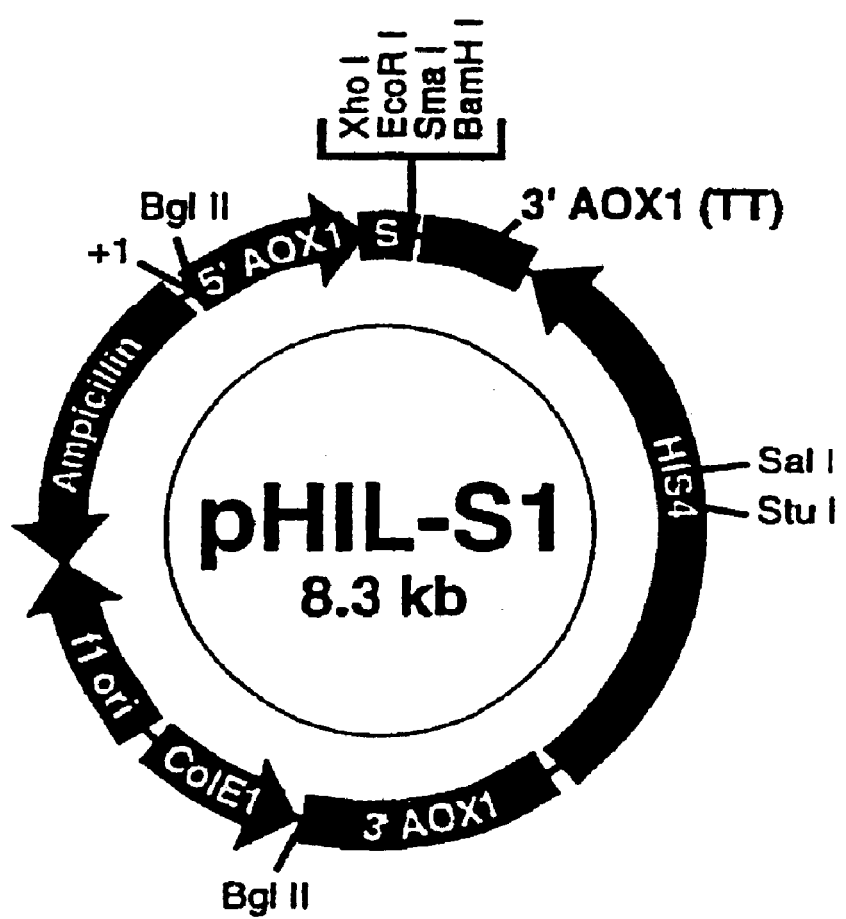
FIG. 2 represents the structure of pPHIL-S1 used as the expression vector for MK protein. The vector comprises *Pichia* yeast alcohol oxidase gene promoter (5' AOX1), signal sequence (S) of *Pichia* yeast acidic phosphatase (PHO1), DNA sequence (3' AOX1-TT) for AOX1 gene transcription termination, and 3' AOX1, which is, together with 5' AOX1, involved in the site-specific integration into the *Pichia* yeast chromosomal DNA, including a multicloning site immediately downstream of the signal sequence. The vector comprises the replication origin of ColE1 and that of bacteriophage f1 for its replication initiation in *E. coli*, and ampicillin resistance gene (Ampicillin) and *Pichia* yeast histidinol dehydrogenase gene (HIS4) as the selection markers.

The expression vector PHIL-S1 (PHILLIPS PETROLEUM Co.) (FIG. 2) comprising the signal sequence of PHO1 (FIG. 1) was used. The vector comprises AOX1 promoter, signal sequence of PHO1, multicloning site in the sequence, HIS4 gene and ampicillin resistance gene as the selection markers, and other sequences. PCR was preformed to amplify the mature MK cDNA using cDNA encoding human MK protein (SEQ ID NO: 1) as the template, and the sense PCR primer (SEQ ID NO: 3) and antisense primer (SEQ ID NO: 4) that contained restriction enzyme EcORI recognition site. MK cDNA was completely digested with the restriction enzyme EcORI, and inserted into the EcORI site of the expression vector pHILS1 which had been digested with EcORI and dephosphorylated with phosphatase to obtain the MK protein expression vector "pHILS1-3AhMK". *Escherichia coli* strain HB101 was transformed with the expression vector. Several clones of the transformed *Escherichia coli* were selected. Using the expression vector contained in these clones as the template and a set of appropriate primers, PCR was carried out to confirm that the inserted cDNA was oriented in the right direction. Furthermore, nucleotide sequences of the MK cDNA and the region near the insertion site thereof on the expression vector were determined to confirm the absence of any errors in the nucleotide sequence. Even though normally processed from the expression vector pHILS1, the mature MK protein possesses three excessive amino acid residues at its amino terminus.

(3) Construction of expression vector comprising the α1 factor secretion signal sequence (part 1)

Figure 4:
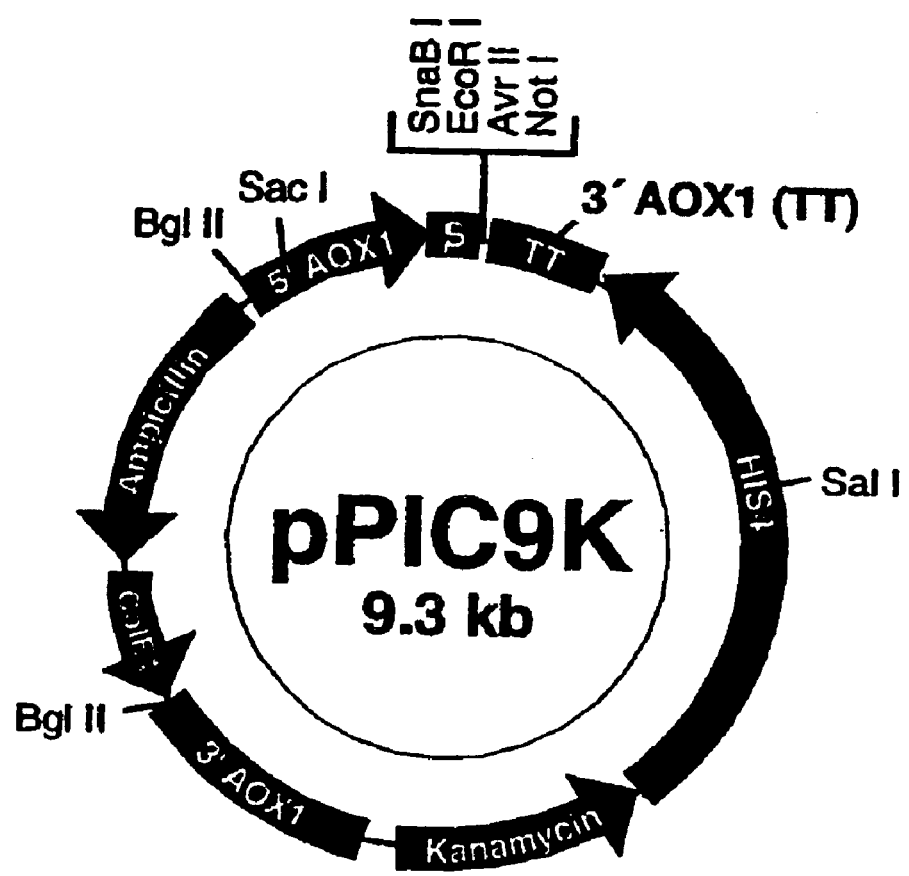
FIG. 4 represents the structure of pPIC9K used as the expression vector for MK protein. The vector comprises *Pichia* yeast alcohol oxidase gene promoter (5' AOX1), signal sequence (S) of α1 factor derived from *Saccharomyces cerevisiae*, DNA sequence (3' AOX1-TT) for AOX1 gene transcription termination, and 3' AOX1, which is, together with 5' AOX1, involved in the site-specific integration into *Pichia* yeast chromosomal DNA, including a multicloning site immediately downstream of the signal sequence. The vector comprises the replication origin of colE1 as that in *E. coli*, and ampicillin resistance gene (Ampicillin), *Pichia* yeast histidinol dehydrogenase gene (HIS4), and kanamycin resistance gene (Kanamycin) as the selection markers.

The expression vector pPIC9K (FIG. 4) comprising a secretion factor signal sequence of the α-pheromone gene (MFα1) from *Saccharomyces cerevisiae* (hereafter referred to as "α1 factor secretion signal") (FIG. 3) was used. The expression vector further comprises the kanamycin resistance gene for the multi-copy selection by G418 in the above-described expression vector pHILS1. According to the above-described method (2), MK cDNA was inserted into the expression vector pPIC9K to obtain the MK protein expression vector "pPIC9K-4AhMK". Even though normally processed from the expression vector, the mature MK protein possesses four excessive amino acid residues at its amino terminus.

(4) Construction of expression vector comprising the α1 factor secretion signal sequence (part 2)

Figure 5:
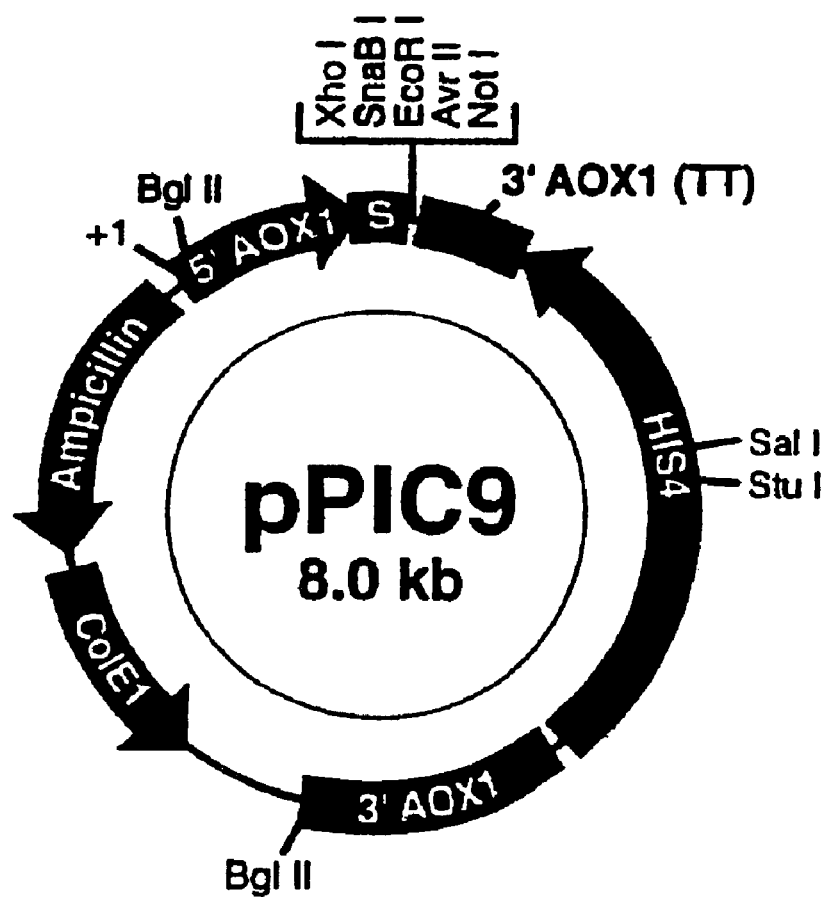
FIG. 5 represents the structure of pPIC9 used as the expression vector for MK protein. The vector comprises *Pichia* yeast alcohol oxidase gene promoter (5' AOX1), signal sequence (S) of α1 factor derived from *Saccharomyces cerevisiae*, DNA sequence (3' AOX1-TT) for AOX1 gene transcription termination, and 3' AOX1, which is involved, together with 5' AOX1, in the site-specific integration into *Pichia* yeast chromosomal DNA, and also includes a multicloning site immediately downstream of the signal sequence. The vector comprises the replication origin of colE1 as that in *E. coli*, and ampicillin resistance gene (Ampicillin) and *Pichia* yeast histidinol dehydrogenase gene (HIS4) as the selection markers.

The expression vector pPIC9 (FIG. 5) comprising the α1 factor secretion signal was used. The mature MK cDNA to be inserted into pPIC9 was prepared in a similar way as described in (2) using a set of sense PCR primer (SEQ ID NO: 5) and antisense PCR primer (SEQ ID NO: 4).

MK cDNA thoroughly digested with restriction enzymes EcORI and XhoI was inserted into the expression vector pPIC9 that had been digested similarly and dephosphorylated with phosphatase to obtain the MK protein expression vector "pPIC9DP-hMK".

EXAMPLE 2

Transformation of *Pichia* yeast with MK Protein Expression Vector

Transfer of the MK protein expression vector into *Pichia* yeast strains GS115 and SMD1168 war carried out according to the protocol for electroporation provided by Invitrogen (for example, pPICZAα, B, and C, Version A, 160410, 25-0150). SMD1168 is a pep4⁻ strain with the reduced protease activity.

Four kinds of MK protein expression vectors, pHILD4-hMK, pHILS1-3AhMK, pPIC9K-4AhMK, and pPIC9DP-hMK, were thoroughly digested with the restriction enzyme SacI or BglII. After washing with distilled water and 1 M sorbitol, GS115 or SMD1168 cells at the early logarithmic growth phase were suspended in 1 M sorbitol, and the expression vector was added thereto. Using a GenePulser of Bio-Rad, electroporation was performed under the conditions of 1.5 kV, 25 µF, and 200–400 Ω. Transformants were selected first by the non-histidine requiring growth, and, if necessary, further by the G418 resistance. Through these selections, MK protein-expressing strains, pHILD4-hMK/GS115, pHILS1-3AhMK/GS115, pPIC9K-4AhMK/GS115, or pPIC9DP-hMK/SM116B transformed with expression vectors; pHILD4-hMK, pHILS1-3AhMK, pPIC9K-4AhMK, or pPIC9DP-hMK, respectively, were obtained.

EXAMPLE 3

Culture of MK Protein-Expression Strains in Test Tube or Flask

The strains were cultured for one day in a completely synthetic medium, which was developed for high cell density fermentation, containing glycerol as the carbon source. Cells were once sedimented by centrifugation, and suspended in a fresh medium containing 1% methanol to induce the expression of MT protein. Methanol (1%) was added everyday with the adjustment of pH to 5 or 3, and the expression induction was continued for 3 days.

(1) Difference in the expression level due to secretion signals

Expression levels of K protein in test tube culture supernatants of expression strains, pHILD4-hMK/GS115, pHILS51-3AhMK/GS115, or pPIC9K-4AhMK/GS115 were examined. In the case of pHILS1-3AhMK/GS115, the expression level of MK protein was extremely low, that is, about 0.1 mg/L at most. In the case of the expression strain pHILS4-hMK/GS115, the secretion of 2 to 3 mg/L was observed for cells with the highest expression level. In contrast, in the case of the expression strain pPIC9K-4AhMK/GS115, the expression level reached 10 mg/L for cells with the highest expression level. These results clearly show that the use of the α1 factor signal sequence can yield about 3 to 5 fold higher expression level of MK protein as compared with the case of using the secretion signal sequence unique to MK protein. The results are summarized as follows.

|  | Secretion signal | MK family | Expression level |
|---|---|---|---|
| PHILD4-hMK | MK | MK | 2–3 mg/L |
| PHILS1-3AhMK | PHO1 | MK | 0.1 mg/L |
| pPIC9K-4AhMK | α1 factor | MK | 10 mg/L (host: GS115) |

(2) Difference in expression products due to pH at the time of expression

The expression strain pPIC9K-4AhMK/GS 115 was allowed to express the protein at pH 3 and 5. Culture supernatants were analyzed by SDS polyacrylamide gel electrophoresis (SDS-PAGE). The multigel 10/20 (Daiichi Pure Chemicals, Co., Ltd.) was used as the gel plate. MK protein on the third day of culturing for expression was recognized as two bands on the gel, the band of smaller molecular weight was major at pH 5, while the upper band of larger molecular weight was predominant at pH 3. These results indicate a less degradation of MK protein at pH 3 than pH 5.

(3) Difference in expression products due to host variety

Expression of MK protein was examined in the expression strains pPIC9K-4AhMK/GS115 and pPIC9DP-hMK/SMD1168. SDS-PAGE of the three-day expression culture supernatants clearly showed MK protein as two bands in the case of pPIC9X-4AhMK/GS115, while only one band was observed in the case or pPIC9DP-AhMK/SMD1168. The results indicate that, in the case where SMD1168, a strain with a low protease activity, is used as the host, degradation of MK protein is kept low.

EXAMPLE 4

Culture of MK Expression Strains in Fermentor

Figure 6:
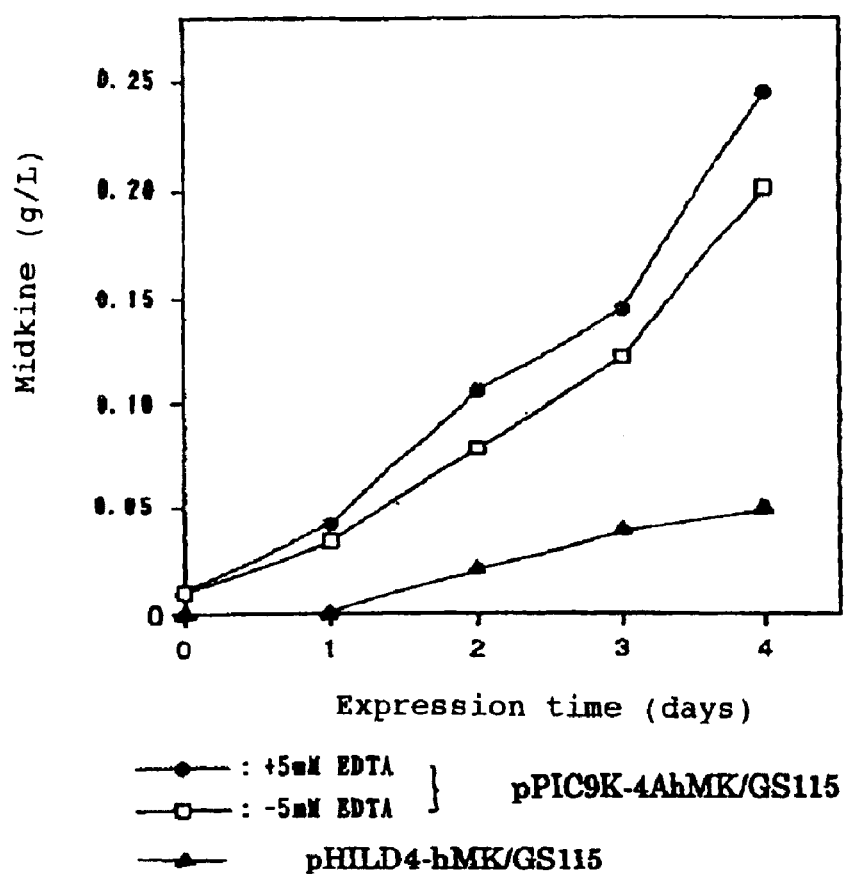
FIG. 6 represents the results of ELISA assay for the expression level of MK protein in the supernatant of fermentor culture of the MK protein expression strain pPIC9K-4AhMK/GS115 (comprising an α1 factor signal sequence derived from *Saccharomyces cerevisiae*) in the presence or absence of 5 mM EDTA, and the expression level of MK protein in the supernatant of fermentor culture of the strain pHILD4-hMK/GS115 (comprising the secretion signal sequence unique to MK protein).
Figure 7:
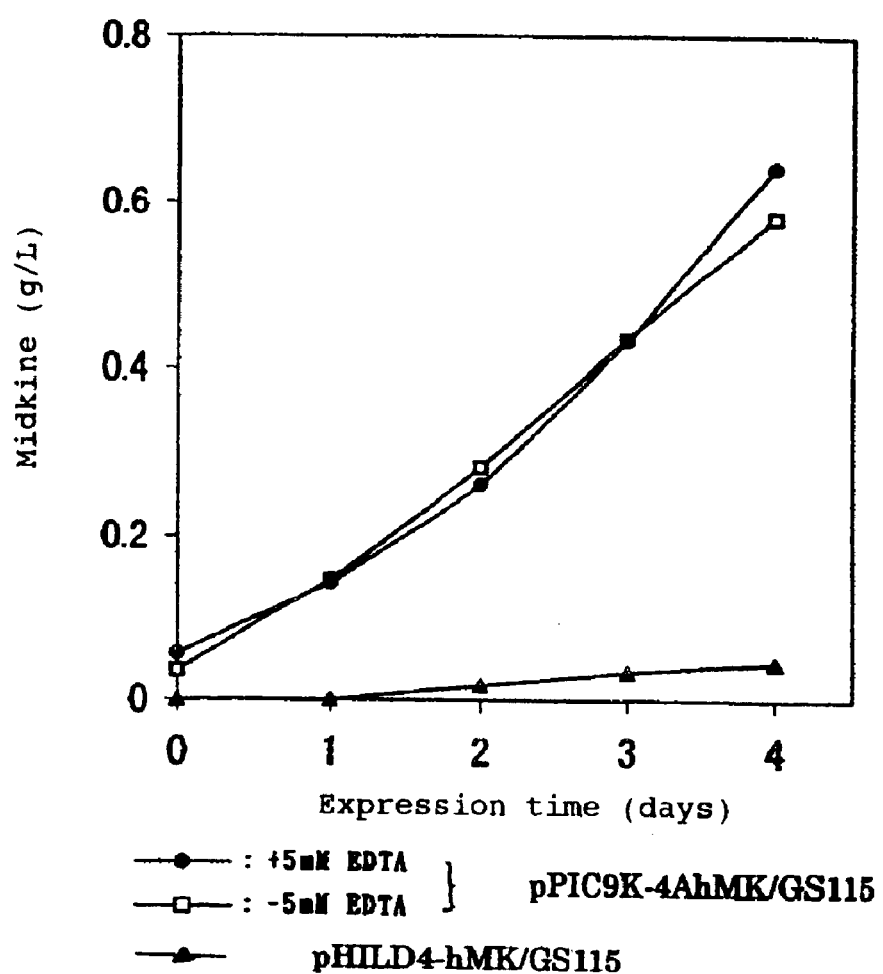
FIG. 7 represents the results of FPLC measurement of the expression level of MK protein in the culture supernatant measured in FIG. 6.

The expression strains pHILD4-hMK/GS115 and pPIC9K-4AhMK/GS115 were cultured in a fermentor according to the method of J. J. Clare et al. (BIO/TECHNOLOGY, Vol. 9,455–460, 1991). In this case, pH during the cell proliferation was set at 4, and the culture temperature at the time of protein expression was at 20° C. MK protein in the culture supernatant on the fourth day of culturing for expression was assayed by ELISA (according to JP-A Hei 10-160735). In the case of pHILD4-hMK/GS115, the expression level of MK protein was 30 to 50 mg/L, while, in the case of pPIC9K-4AhMK/GS115, it was about 200 mg/L, and, furthermore, the expression level was elevated to about 240 mg/L by addition of EDTA to the medium (FIG. 6). When expression level of MK protein for the same samples was determined by FPLC analysis using a Hitrap-Heparin column (Pharmacia, 1 ml) (0 to 2 M NaCl in 50 mM Tris-HCl, pH 7.5, flow rate 1 ml/min) measuring the absorbance at 280 nm (with the chemically synthesized mature MK protein purchased from Peptide Institute as the standard substance), the expression level of pHILD4-hMK/GS115 was about 50 mg/L and that of pPIC9K-4AhMK/GS115 was about 580 mg/L, which rose to about 640 mg/L (MK protein 1 mg/mL=1.8 $A_{280}$) when EDTA was added (FIG. 7). The results indicate that, in the case of culture in a fermentor similarly as in the case of culture in test tubes, use of α1 factor signal sequence increased the expression level of PM protein about 5 to 8 fold as compared with the case where the secretion signal sequence unique to MK protein was used. In addition, from the analytical results of the culture supernatant by SDS-PAGE and western blot, it has become evident that the main protein in the culture supernatant is the human MK protein which has been produced through secretory expression.

EXAMPLE 5

Analysis of Purified MK Protein (part 1)

From the fermentor culture supernatant of pPIC9-4AhMK/GS115, MK protein was purified using SP-Sepharose and heparin Sepharose.

The culture supernatant (10 ml) was collected, and diluted with an equal volume of distilled water. The solution was adjusted to pH 5 with ammonia, and applied to a STREAMLINE SP column (about 1 ml) (Pharmacia) equilibrated with 60 mM acetate buffer (pH 5.2). After adsorption, the column was washed with the buffer containing 0.5 M NaCl, and then, MK protein was eluted with the buffer containing 2 M NaCl. The eluate was dialyzed against 50 mM Tris-HCl (pH 7.5). The dialyzed sample was applied to a column of STREAMLINE Heparin (about 0.5 ml) (Pharmacia) equilibrated with the above-described buffer used for dialysis, and, after washing the column with the above-described buffer containing 0.5 M NaCl, MK protein was eluted with the above-described buffer containing 2 M NaCl. The eluate was dialyzed against distilled water to obtain the purified MK protein.

Mass spectrometry of the purified MK protein was performed by the MALDI method. A mass spectrometer used was VOYAGER ELITE (PerSeptive Biosystems). Sinapinic acid (10 mg/mL acetonitrile/water/TFA=33/67/0.1) was used as the matrix. A dried sample was dissolved in water (30 μL), the matrix solution (9 volumes) was added to the dissolved sample, and the resulting solution (1 μL) was applied to sample plates for use. Calibration was carried out with ubiquitin (+1): 8565.89 (average) and myoglobin (+1): 16952.56 (average) as the standard proteins.

Amino acid sequence analysis of the amino terminus was performed by the Edman method. A protein sequencer used was PPSQ21 (Shimadzu).

Figure 8:
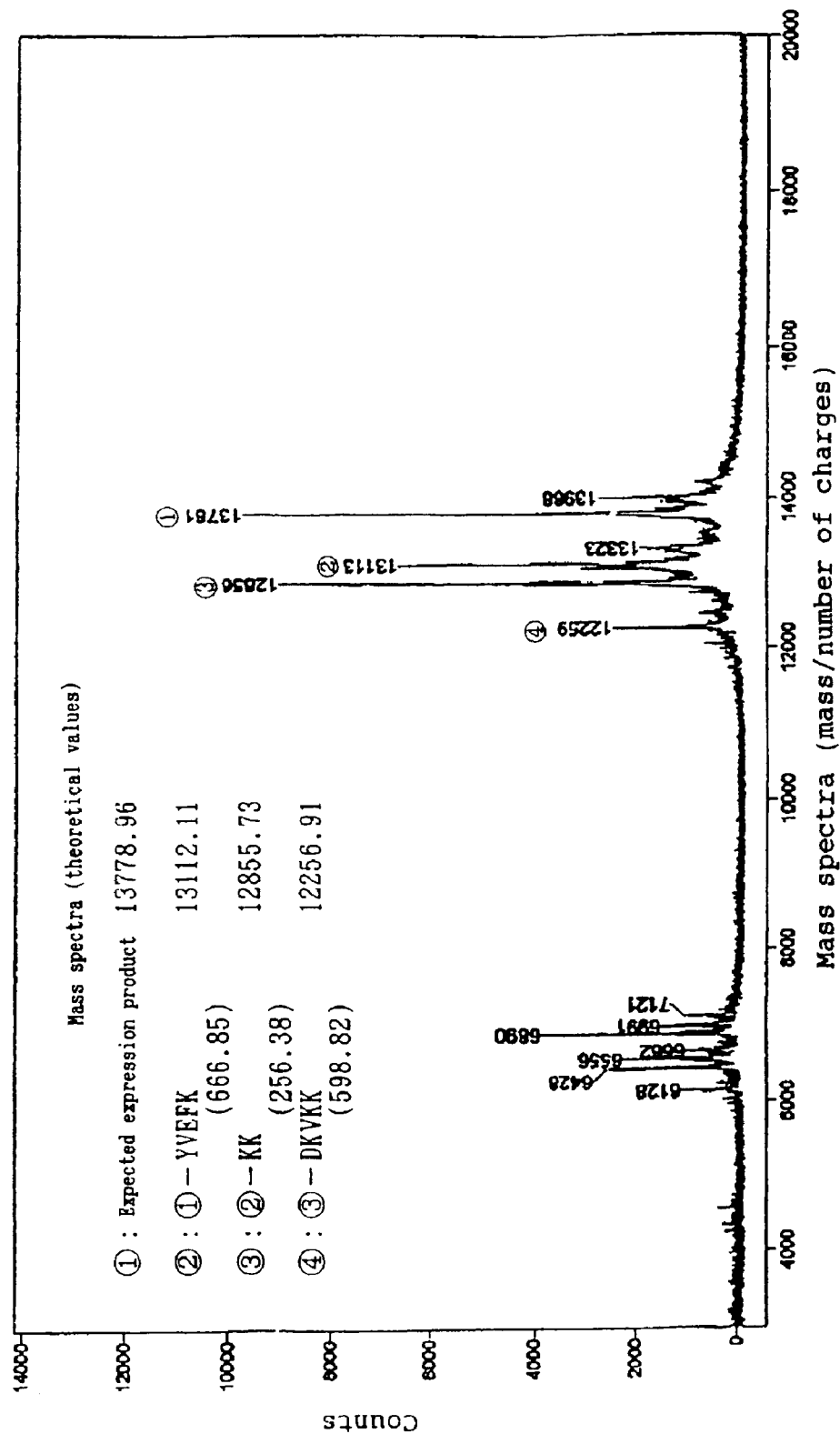
FIG. 8 shows the results of MALDI mass spectrometry of MK protein purified from the culture supernatant of the MK protein expression strain pPIC9K-4AhMK/GS115 (comprising an α1 factor signal sequence derived from *Saccharomyces cerevisiae*).

In mass spectrometry of the purified MK protein, besides the expected MK protein (mature MK protein with Tyr-val-Glu-Phe added to its N-terminus), proteins with deletions of 5 amino acids Tyr-val-Glu-Phe-Lys, 7 amino acids Tyr-val-Glu-Phe-Lys-Lys-Lys, and 12 amino acids Tyr-val-Glu-Phe-Lys-Lys-Lys-Asp-Lys-val-Lys-Lys, from the N-terminus were observed (FIG. 8). In addition, as a result of the N-terminal analysis of the expressed MK protein, Tyr, Lys, and Asp were detected, and they coincided with the amino acids at the N-termini of proteins with deletions of the above-described five amino acids and seven amino acids from the N-terminus of the expected expression product MK protein. Furthermore, no obvious signals for glycosylated MK are observed. From these results, it is evident that MK protein thus expressed is not glycosylated.

It is obvious that, as compared with the ease where the signal sequence unique to MK is employed, use of the α1 factor signal sequence leads to a remarkable increase in the expression level of MK protein, and an extremely few yeast-specific glycosylation to the expression product.

EXAMPLE 6

Analysis of the Purified MK Protein (Part 2)

Figure 9:
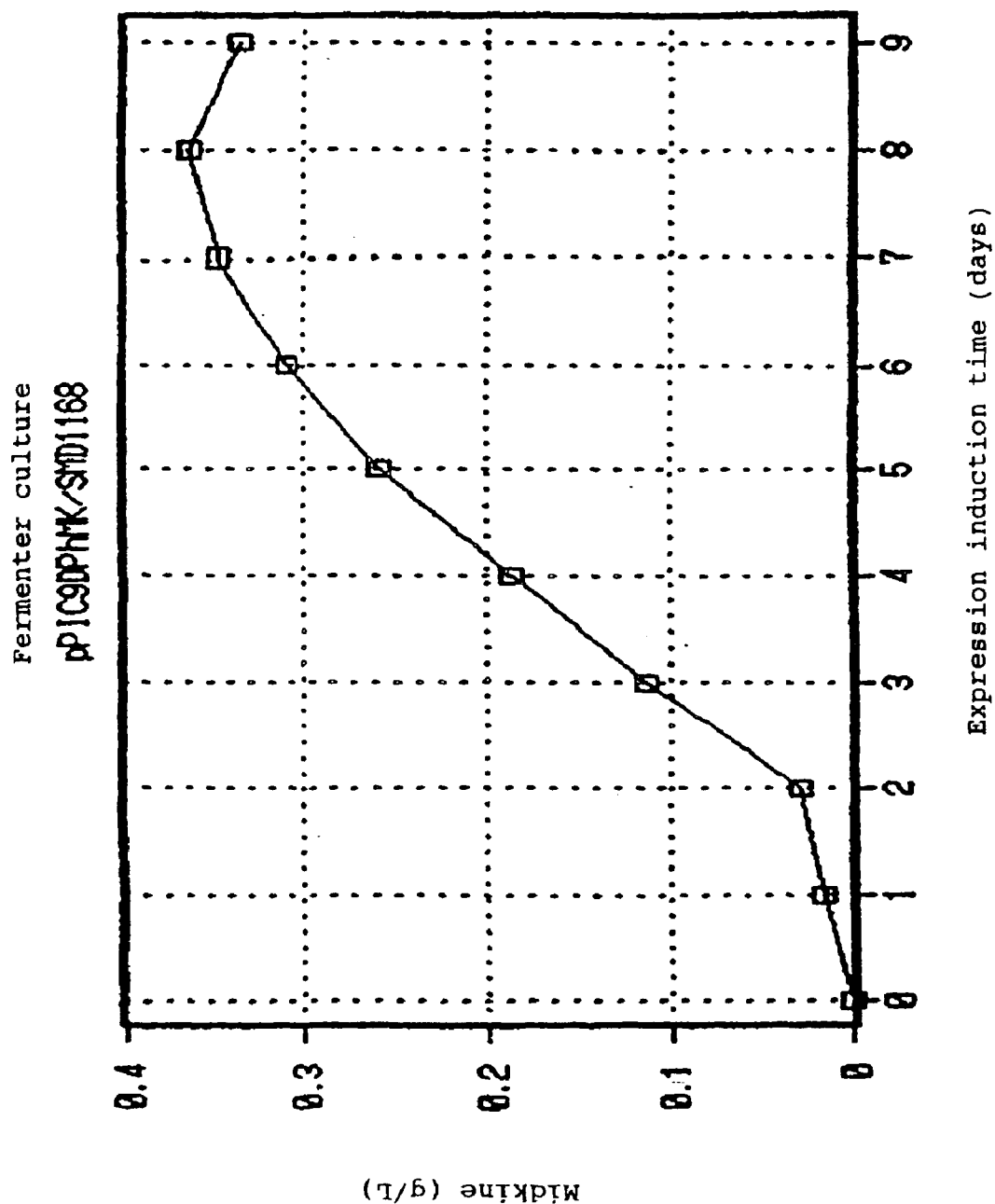
FIG. 9 represents the results of FPLC measurement of the expression level of MK protein purified from the fermentor culture supernatant of the MK protein expression strain pPIC9DP-hMK/SMD1168 (comprising an α1 factor signal sequence derived from *Saccharomyces cerevisiae*).

Expression strain pPIC9DP-hMK/SMD1168 obtained in Example 2 was cultured in a fermentor. Although the culture was carried out basically according to the method described in Example 4, cell proliferation using glycerol was continued until the cell density became about $A_{600}$=100, and then methanol addition was initiated to simultaneously perform the cell proliferation and expression induction. Temperature and pH at the time of protein expression were set at 20° C. and 3, respectively. Expression induction was continued for nine days. The expression level of MK protein measured by FPLC reached maximum (360 mg/L) on the eighth day of culture (FIG. 9). MK protein was purified from 10 ml of the culture supernatant on the seventh day using SP Sepharose and Heparin Sepharose as in Example 5. Separately, purification by FPLC using a Hitrap-Heparin column (Pharmacia, 1 ml) was also performed with elution by a linear gradient of NaCl in 50 mM Tris-HCl (pH 7.5).

The expressed MK protein and chemically synthesized mature MK protein (Peptide Institute) as the standard were compared by performing the reduced SDS-PAGE, non-reduced SDS-PAGE, and native-PAGE, and no difference in the measured results including molecular weight was observed. Although native-PAGE was carried out according to the method of Davis, electrodes in the electrophoresis bath were reversely connected because of the high isoelectric point of the protein of interest. Amino acid sequence at the amino terminus of the expressed MK protein matched that of mature MK protein as shown in Table 1.

TABLE 1

Analytical results of amino acid sequence at the amino terminus of expression products

| Analysis cycle | Sort of amino acid | Amount of amino acid (pmol) |
| --- | --- | --- |
| 1 | Lys | 114 |
| 2 | Lys | 119 |
| 3 | Lys | 132 |
| 4 | Asp | 109 |
| 5 | Lys | 125 |
| 6 | Val | 137 |
| 7 | Lys | 123 |
| 8 | Lys | 121 |
| 9 | Gly | 94 |
| 10 | Gly | 94 |

In addition, the sample was dissolved in 100 μL of pure water, an aliquot (50 μL) thereof was taken in a glass test tube, to which 50 μL of concentrated hydrochloric acid was added, and then the mixture was subjected to hydrolysis in a vacuum sealed tube at 110° C. for 22 hr. The sample was evaporated to dryness, dissolved again in 75 μL of pure water, and aliquot (50 μL) thereof was subjected to amino acid composition analysis by the amino acid analytical method using Hitachi amino acid analyzer L8500. The results are shown in Table 2.

TABLE 2

Result of amino acid composition analysis of expression product (MK)

| Amino acid | Expected | hMK (standard) (Peptide Institute) | rhMK (pPIC9DP-hMK/SMD1168) |
| --- | --- | --- | --- |
| Asx | 8 | 7.66 | 7.70 |
| Thr | 10 | 9.51 | 9.59 |
| Ser | 3 | 2.81 | 2.78 |
| Glx | 11 | 11.22 | 11.37 |
| Gly | 16 | 16.00 | 16.00 |
| Ala | 10 | 9.96 | 10.03 |
| Val | 5 | 4.88 | 4.89 |
| Cys | 10 | n.d. | n.d. |
| Met | 0 | 0.00 | 0.00 |
| Ile | 2 | 1.85 | 1.93 |
| Leu | 1 | 0.98 | 1.01 |
| Tyr | 2 | 1.93 | 1.73 |
| Phe | 3 | 2.93 | 2.97 |
| Lys | 23 | 22.81 | 22.62 |
| His | 0 | 0.00 | 0.00 |
| Arg | 7 | 6.73 | 6.80 |
| Trp | 4 | n.d. | n.d. |
| Pro | 6 | 6.11 | 5.89 |

Except for Trp, which cannot be measured because of hydrolysis in hydrochloric acid, Cys, the accurate value of which can hardly be obtained, the results show excellent match as compared with the theoretical values of amino acid residues in the chemically synthesized mature MK protein as the standard specimen (Peptide Institute), indicating that MK was obtained with high purity.

Figure 10:
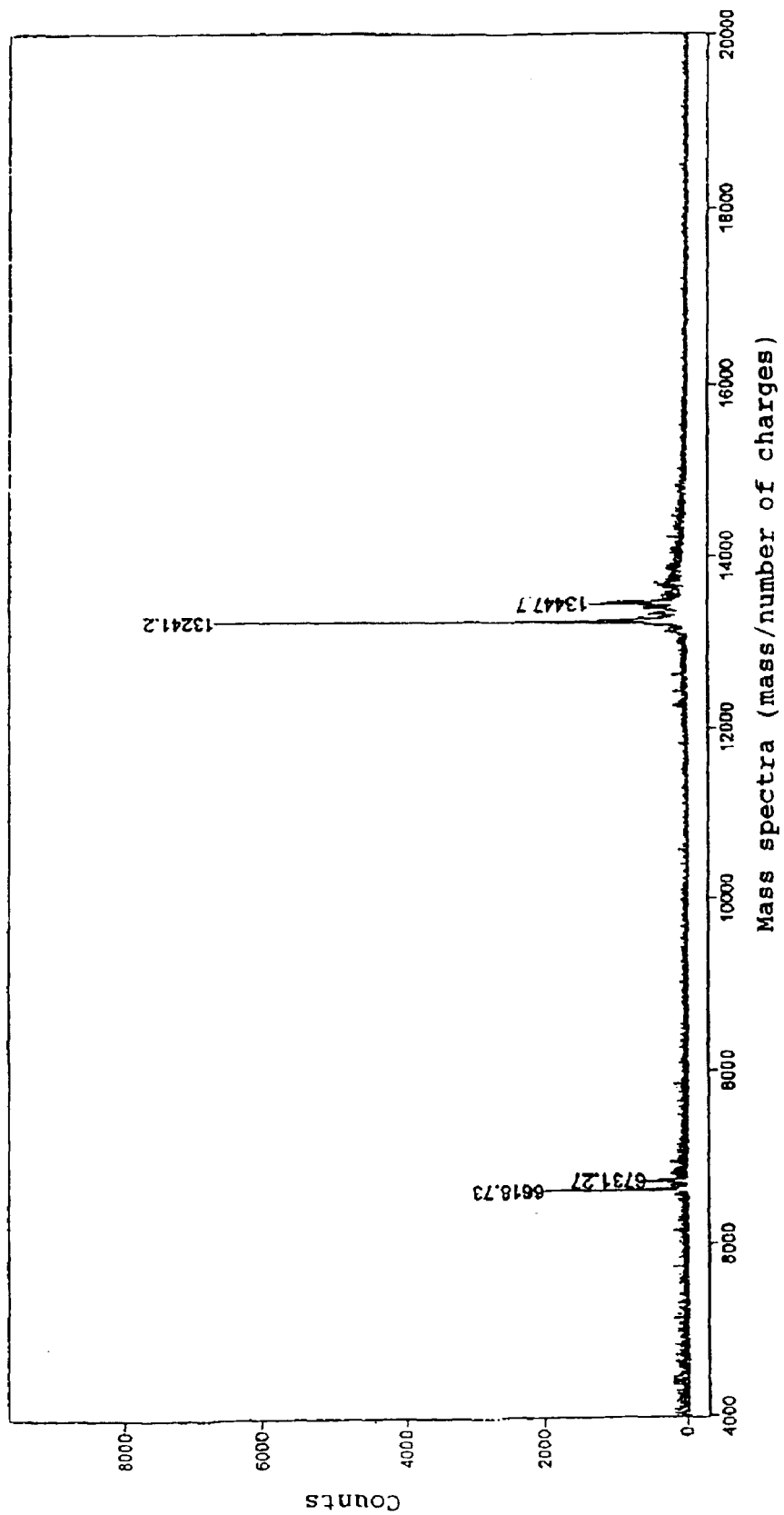
FIG. 10 shows the results of mass spectrometry of MK protein purified from the culture supernatant of the intact MK protein expression strain pPIC9DP-hMK/SMD1168 (comprising an α1 factor signal sequence originating from *Saccharomyces cerevisiae*).
Figure 11:
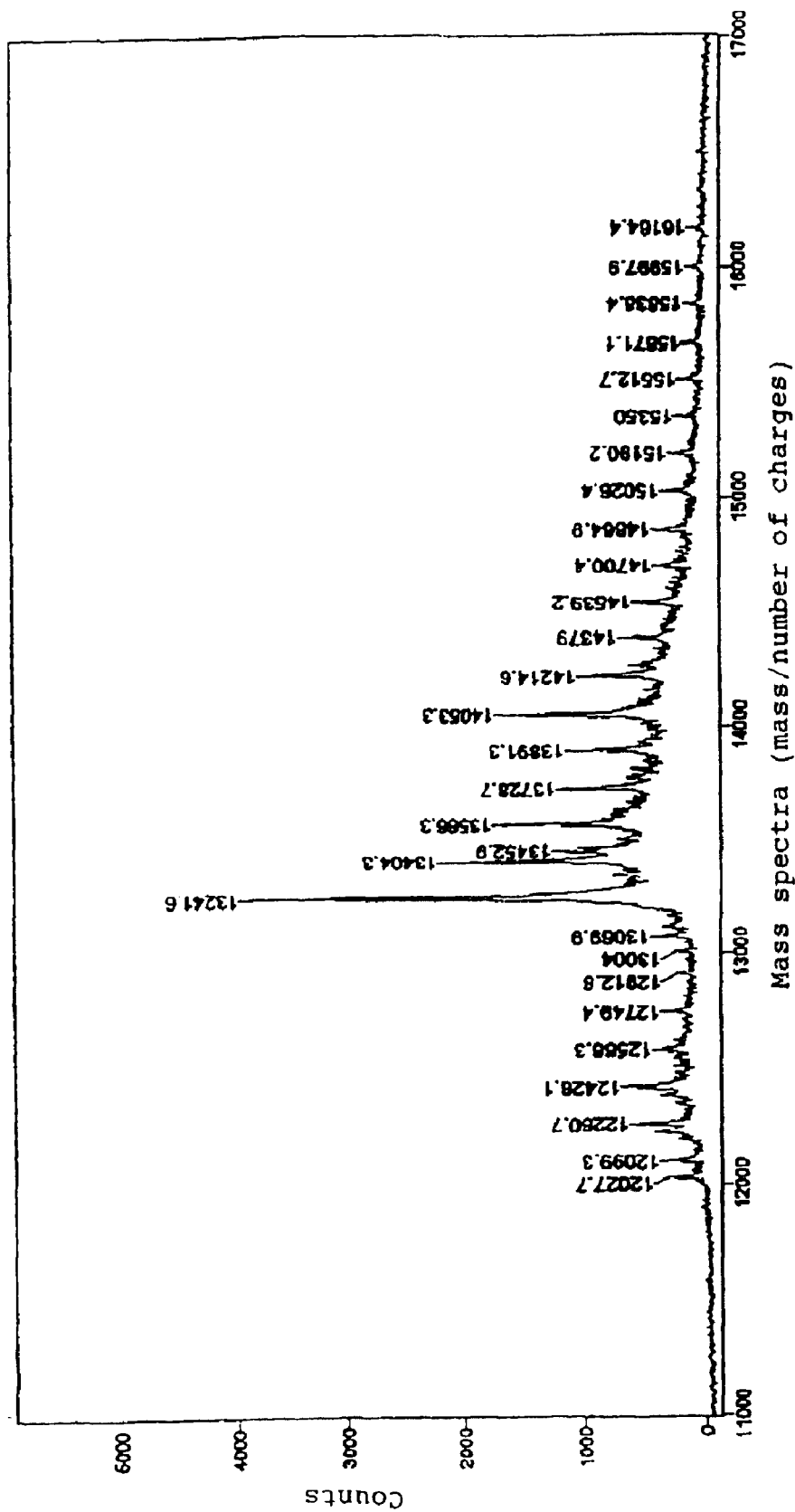
FIG. 11 shows the results of mass spectrometry of MK protein purified from the fermentor culture supernatant of the expression strain pHILD4-hMK/GS115.

The value obtained in mass spectrometry was 13241.2 (+1 value), which is almost the same as the expected value of the molecular weight (theoretical value (+1) is 13241.3) (FIG. 10), and, furthermore, only a minute amount of degradation products were formed by altering the host from GS115 to SMD1168 and changing culture conditions as compared with the case of pPIC9K-4AhMK/GS115. No signal for glycosylation of MK was observed. For comparison, results of mass spectrometry of purified MK protein which was expressed by culturing the expression strain containing the signal sequence unique to MK (pHILD4-hMK/GS115) are shown in FIG. 11. Although the peak of intact MK is the highest (13241.6), peak for MKs which are thought to be associated with 1 to 18 sugar molecules are also observed. Peaks with mass numbers smaller than that of intact MK are thought to represent partially degraded MKs. Since intact MK protein can be obtained only in a limited ratio in expressed products, which contain lots of molecular species different only in the number of bound sugars, it is difficult to purify an intact MK family protein from the expression products. Judging from the above-mentioned facts, the majority of the MK family protein obtained herein is unglycosylated intact mature MK protein. Its expression level is also markedly high as compared with the strains so far used. Therefore, by using this expression strain pPIC9DP-hMK/SMD1168 for the secretory production of an MK family protein, it in possible to carry out a high level secretory expression of intact MK protein.

Figure 12:
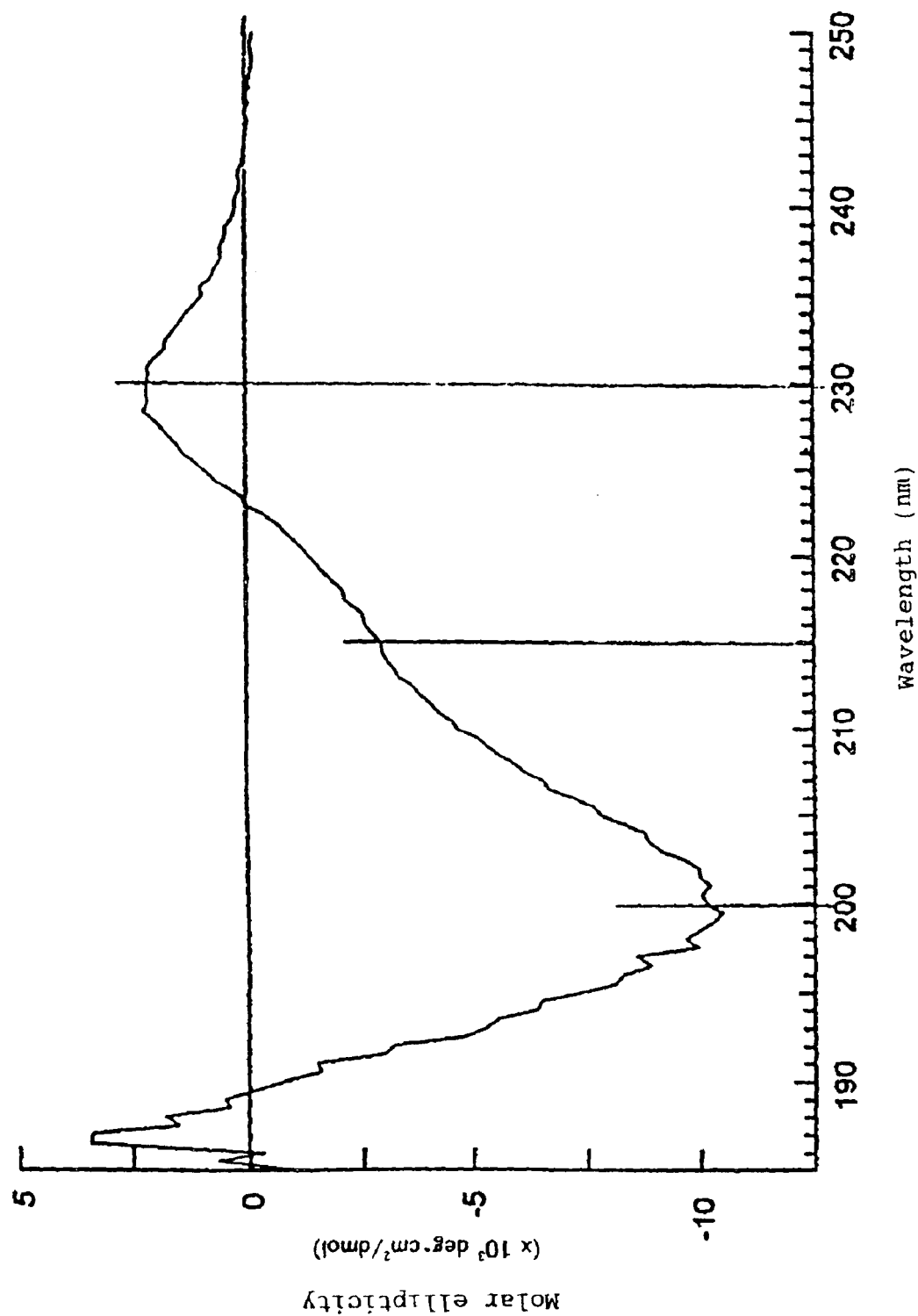
FIG. 12 shows a CD spectrum of MK protein purified from the fermentor culture supernatant of the xpr ssion strain pPIC9DP-hMK/SMD1168.

To obtain information on the secondary structure of intact MK protein thus obtained, its CD spectrum was measured. The results are shown in FIG. 12.

EXAMPLE 7

Biological Activity Assay (1) Growth activity for NIH3T3 fibroblast

Figure 13:
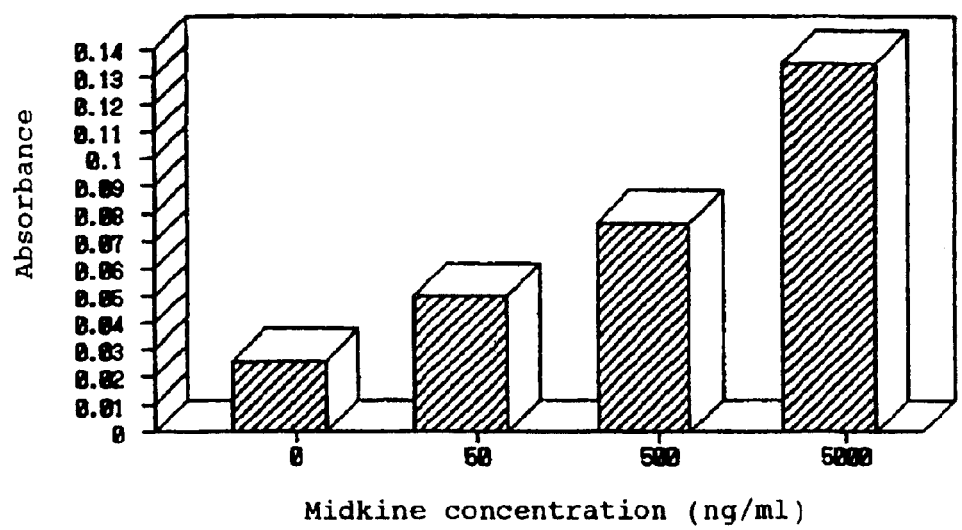
FIG. 13 shows the growth activity of NIH3T3 cells induced by intact MK protein.

Cell proliferation-promoting activity was examined using the established fibroblast strain NIH3T3 derived from fetal Swiss mouse. NIH3T3 cells (2000 cells per well) were placed (onto 96-well cell culture plates, and cultured for 24 hr in Dulbecco's modified Eagle medium (DMEM) supplemented with 10% fetal calf serum (FCS). Then, the whole medium was replaced with a mixed medium consisting of DMEM supplemented with both 10% FCS and 0 to 5000 ng/mL of intact MK (protein concentration determined based on BCA method with BSA as the standard protein) and Ham's F-12 medium (1:1) plus ITS (10 mg/L human insulin, 10 mg/L human transferrin, and 10 μg/L selenous acid), and the culturing was further continued for 2 days. Then, the WST-1 reagent was added to the culture medium, and the absorbance of each well was measured 4 hr later with a plate reader to count viable cells. As a result, it was evident that the viable cell count dose-dependently increased (FIG. 13).

EXAMPLE 8

Construction of PTN Expression Vector

According to Example 1, the human PT protein expression vector "pPIC9-hPTN", containing the α1 factor secretion signal sequence, was constructed. cDNA encoding human mature PTN protein was amplified by PCR using PTN cDNA (SEQ ID NO: 6) as a template and a set of sense PCR primer (SEQ ID NO: 8) and antisense PCR primer (SEQ ID NO: 9) containing the restriction enzyme EcORI recognition site.

EXAMPLE 9

Transformation of *Pichia* Yeast with the PTN Protein Expression Vector

According to Example 2, pPIC9-hPTN was transferred to *Pichia* yeast strain GS115 to obtain the PA protein expression strain pPIC9-hPTN/GS115.

EXAMPLE 10

Expression of PTN Protein

Figure 14:
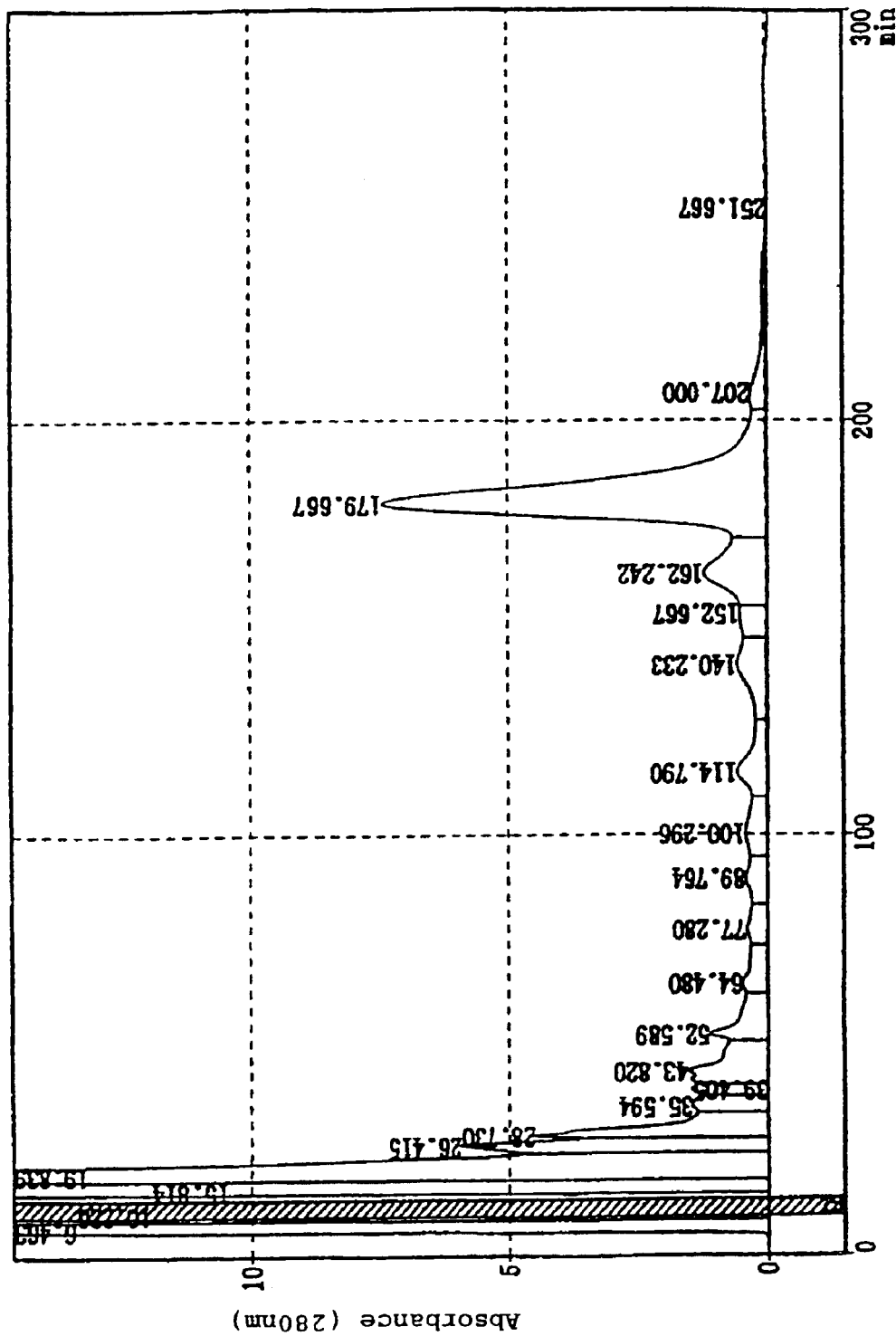
FIG. 14 shows an HPLC (PolySULFOETYLA; Poly LC) elution profile of the fermentor culture supernatant of the strain pPIC9-hPTN/GS115.

According to the method described in Example 4, pPIC9-hPTN/GS115 was cultured in a fermentor, and the culture supernatant (50 ml) was fractionated using a HPLC column (PolySULFOETYL A, Poly LC). Elution was performed with 0.7 M $Na_2SO_4$–35 mM MPB (phosphate buffer, pH 2.7). Results are shown in FIG. 14. The peaks up to the retention time 30 min and the peaks at 140–162 min are thought to correspond to low molecular weight compounds such as nucleic acid, and glycosylated PTN, respectively, and the peak at 179 min can be regarded as intact PTN protein. From the peak area, the expression level of intact PTN protein is calculated to be about 250 mg/L (PTN protein 1 mg/mL=1.56 $A_{280}$).

EXAMPLE 11

Purification of PTN (1) Purification with STREAMLINE SP—STREAMLINE SP (Amersham/Pharmacia; 300 ml) was added to a column (5×100 cm), and a fluidized bed was prepared by the upward liquid flow. After the column was equilibrated with 20 mM acetate buffer (pH 5.5), a culture solution (4.9 L) diluted 2-fold with water was applied thereto. The column was washed with the upward liquid flow of the same buffer, and washed with the downward liquid flow. Then, elution was performed with 2 M sodium chloride-20 mM acetate buffer (pH 5.5) to obtain 200 ml of the eluted fractions.

(2) Purification by sulfated Cellulofine—A column was packed with 500 ml of the carrier, sulfated Cellulofine m (Seikagaku Kogyo), and equilibrated with 0.4 M sodium chloride—10 mM phosphate buffer (pH 7.2). The above-described SP purification eluate (200 ml) was diluted 3-fold with water, and phosphate buffer was added to the diluted solution to a final concentration of 10 mM. After the resulting solution was adjusted to pH 7.2 with 8 N sodium hydroxide, the solution was applied to the above-described column. After the column was washed with 0.7 M sodium chloride—10 mM phosphate buffer (pH7.2), elution was performed with 2× sodium chloride—10 mM phosphate buffer, pH 7.2, to obtain 195 ml of eluted fractions.

(3) Purification by gel filtration—Two columns (1.3×60 cm each) of Superdex 75 pg (Amersham/Pharmacia) were connected in series, and equilibrated with 0.152 M sodium chloride. The eluted fraction (195 ml) described in (2) above was applied to the column, and elution was performed with the same solution to obtain 200 ml of eluted fractions.

(4) Ion exchange purification—After a column (1×25 cm) of polySULFOETYL A (polyLC) was equilibrated with 0.6 M sodium chloride—20 mM acetate buffer (pH 5.5), the above-described gel filtration eluate (50 ml) was applied to the column, which was washed with 0.88 M sodium chloride—20 mM acetate buffer (pH 5.5). Just prior to the elution with the same buffer, the buffer was replaced by 2 M sodium chloride—20 mM acetate buffer (pH 5.5) to obtain 20 ml of concentrated eluted fractions. The same process was repeated four times. Results of purification are shown in Table 3.

TABLE 3

Purification of recombinant human pleiotrophin (rhPTN)[1]

| | Volume (ml) | rhPTN (mg)[2] | Purity (%)[3] | Yield (%) |
|---|---|---|---|---|
| Expanded bed | 200 | 950 | 63 | 96 |
| Sulfated Cellulofine | 195 | 840 | 70 | 85 |
| Gel filtration | 200 | 828 | 74 | 84 |
| PolySULFOETHYL A | 80 | 713 | 90 | 72 |

[1]Results of purification from 4.9 L of the culture medium of *Pichia* yeast.
[2]Quantitated by HPLC.
[3]Expressed as the percent absorbance at 280 nm measured by HPLC.

EXAMPLE 12

Analysis of Purified PTN Protein Amino Terminal Analysis

As shown in Table 4, the amino-terminal amino acid sequence of the purified PTN coincided with that of the standard intact PTN protein.

TABLE 4

Analytical results of the N-terminal amino acid sequence of expression product (PTN)

| Analysis cycle | Amino acid | Amount of amino acid (pmol) |
|---|---|---|
| 1 | Gly | 95 |
| 2 | Lys | 111 |
| 3 | Lys | 111 |
| 4 | Glu | 96 |
| 5 | Lys | 112 |
| 6 | Pro | 75 |
| 7 | Glu | 58 |
| 8 | Lys | 74 |
| 9 | Lys | 86 |
| 10 | Val | 67 |

Amino Acid Composition

As shown in Table 5, in the amino acid composition of the purified PTN, the expected values were almost identical to the experimental values. In this case, no degradation of cysteine due to acid hydrolysis was observed.

TABLE 5

Analytical results of amino acid composition of expression product (PTN)

| Amino acid | Expected | rhPTN (pPIC9-hPTN/GS115) |
|---|---|---|
| Asx | 7 | 6.40 |
| Thr | 12 | 11.25 |
| Ser | 6 | 5.37 |
| Glx | 20 | 19.79 |
| Gly | 12 | 11.74 |
| Ala | 7 | 6.83 |
| Val | 4 | 3.89 |
| Cys | 10 | 9.67 |
| Met | 2 | 1.85 |
| Ile | 2 | 1.89 |
| Leu | 7 | 6.78 |
| Tyr | 1 | 0.97 |
| Phe | 2 | 1.95 |
| Lys | 28 | 28.21 |
| Trp | 4 | — |

TABLE 5-continued

Analytical results of amino acid composition of expression product (PTN)

| Amino acid | Expected | rhPTN (pPIC9-hPTN/GS115) |
|---|---|---|
| His | 1 | 1.08 |
| Arg | 5 | 4.63 |
| Pro | 6 | 5.90 |

Mass Spectrometry

Figure 15:
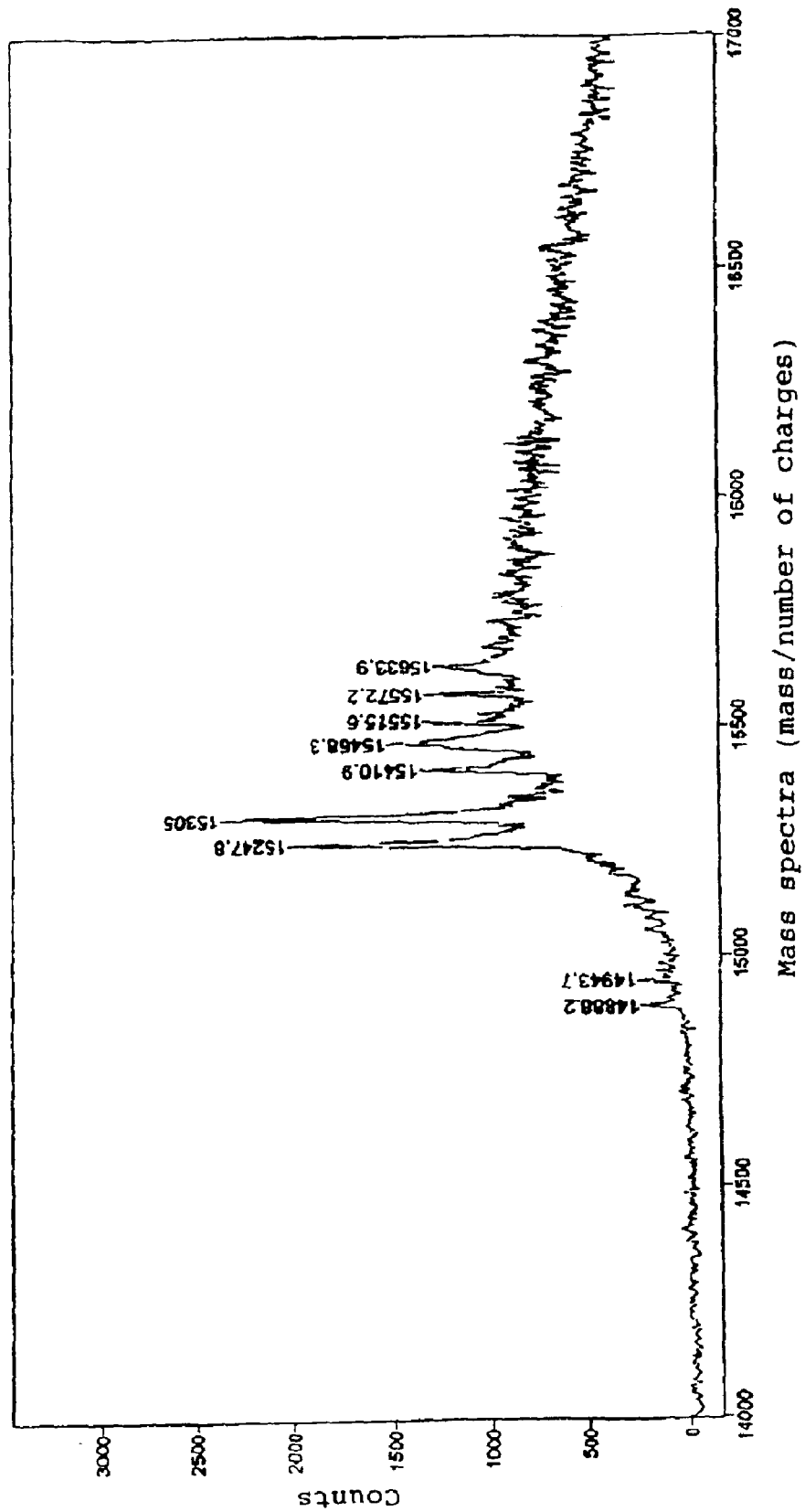
FIG. 15 shows the results of mass spectrometry of human PTN purified from the fermentor culture supernatant of the expression strain pHILD4MK-hPTN/GS115 comprising the secretion signal of human MK.
Figure 16:
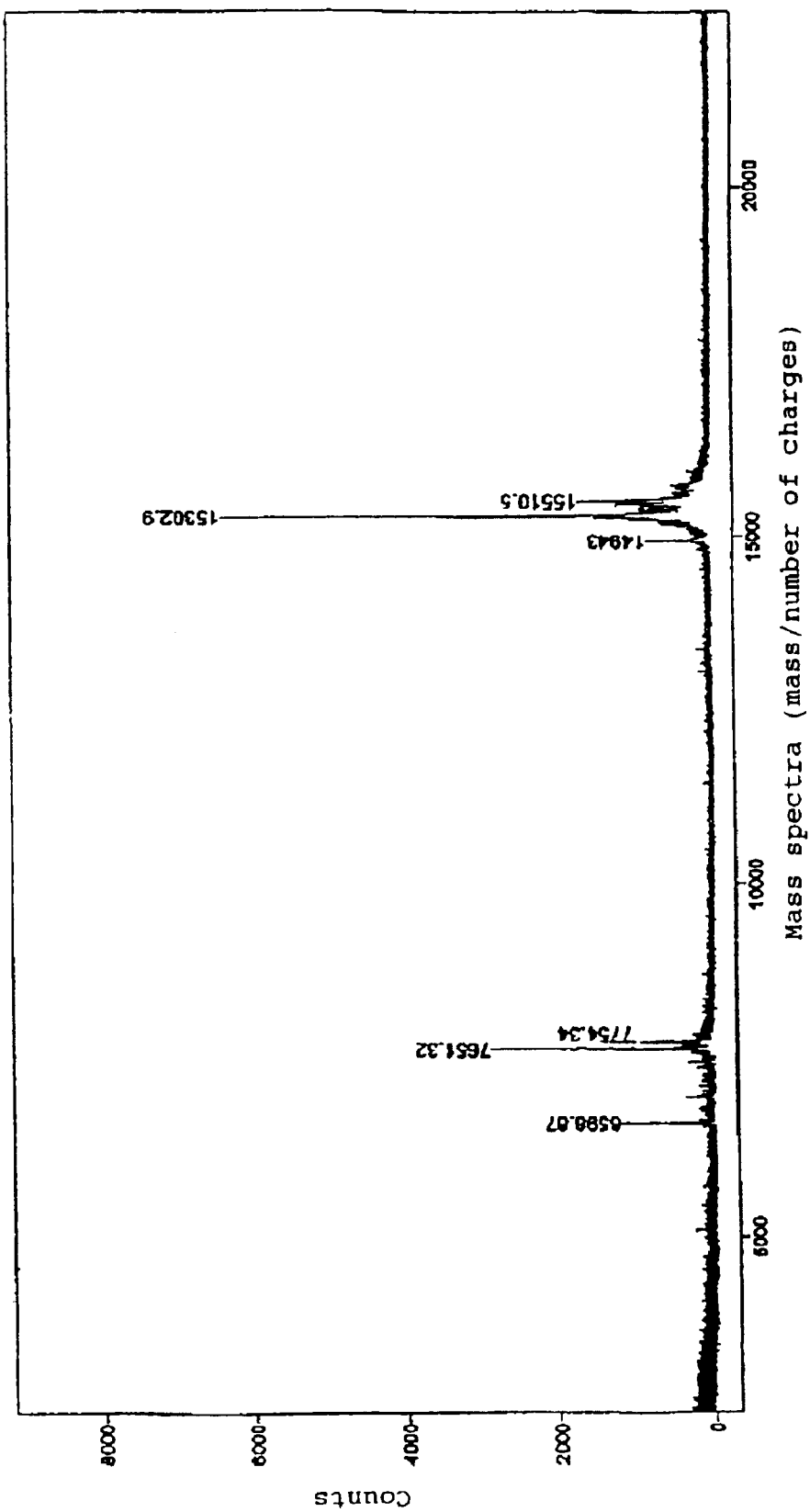
FIG. 16 shows the results of mass spectrometry of human PTN purified from a fermentor culture supernatant of the expression strain pPIC9-hPTN/GS115.

Results of mass spectrometrical analysis by the MALDI method of purified pleiotrophin which was expressed using a human midkine secretion signal are shown in FIG. 15. In this case, besides intact pleiotrophin (15305 (+1)), pleiotrophin with Gly at the amino terminus deleted (15247 (+1)), and a large amount of the two glycosylated pleiotrophins are observed (for example, 15410.9 (+1) and 15468.3 (+1)). In contrast to this, as shown in FIG. 16, the pleiotrophin expressed by the expression strain pPIC9-hPTN/GS115 has a main peak (15302.9 (+1)), which is almost the same as the theoretical value of intact pleiotrophin (15303.9 (+1)). The peak at 15510.5 (+1) represents pleiotrophin associated with matrix molecules. Therefore, this expression strain pPIC9-hPTN/GS115 is thought to be suitably used for the secretory production of PTN protein.

CD Spectrum

A purified PTN (6.1 mg/mL) was diluted with saline to a concentration of 0.203 mg/mL, and subjected to the CD spectrometrical analysis using the JASCO J-500A (temperature, room temperature (about 24° C.); wave length range, 200 to 250 nm; cell length, 1 mm; number of integration, 8). As shown in FIG. 11, a negative Cotton effect was observed around 215 nm to indicate the presence of β structure, clearly demonstrating structural similarity to the human midkine. In the analysis of secondary structure (Y. H. Chen, et al., Biochemistry 11, 4120–4131 (1972)), it was found that the ratio of α helix:βhelix: random structure was 1:41:58.

INDUSTRIAL APPLICABILITY

According to the present invention, an intact MK fatally protein can be easily and economically prepared by genetic engineering techniques. Since the intact MK family protein according to this invention is not associated with sugars derived from yeast, it does not pose problems of antigenicity in its administration to mammals such as humans. Therefore, the intact MK family protein of this invention is useful as drug raw materials. Furthermore, since the intact MK family protein according to this invention retains the expected biological activities, it can be said that the protein is of high quality as drug raw materials or research materials for the structural and functional studies on an MK family protein.

What is claimed is:

1. A vector for secretory expression of an intact MK family protein by methylotrophic yeast, said vector comprising a gene encoding a mature MK family protein ligated to a signal sequence of α1 factor from *Saccharomyces cerevisiae*.

2. The vector according to claim 1 comprising components (a) to (g) below:
   (a) a promoter sequence of a methanol-inducible alcohol oxidase gene (AOX1) from *Pichia pastoris*,
   (b) a signal sequence of α1 factor from *Saccharomyces cerevisiae*,
   (c) a gene encoding a mature MK family protein, wherein said gene is ligated to (b),
   (d) a transcription termination sequence of a methanol-inducible alcohol oxidase gene (AOX1) from *Pichia pastoris*,
   (e) a selection marker gene functioning in *Escherichia coli* and methylotrophic yeast,
   (f) a replication origin functioning in *Escherichia coli*, and
   (g) 5' and 3' end sequences of the AOX1 gene, wherein said sequences allow site-specific homologous recombination to a methylotrophic yeast chromosomal DNA to occur.

3. The vector according to claim 1, wherein said MK family protein is MK protein.

4. The vector according to claim 1, wherein said MK family protein is PTN protein.

5. A transformant comprising methylotrophic yeast transformed with a vector for secretory expression of an intact MK family protein, said vector comprising a gene encoding a mature MK family protein ligated to a signal sequence of at factor from *Saccharomyces cerevisiae*, wherein said transformant has increased secretory expression of an intact MK family protein compared to an untransformed yeast.

6. The transformant according to claim 5, wherein said transformant is pPIC9DP-hMK/SMD1168, said MK family protein is MK protein, and said methylotrophic yeast is strain SMD1168.

7. The transformant according to claim 5, wherein said transformant is pPIC9-hPTN/GS115, said MK family protein is PTN protein, and said methylotrophic yeast is strain GS115.

8. A method for producing an intact MK family protein, said method comprising culturing a transformant comprising methylotrophic yeast transformed with a vector for secretory expression of an intact MK family protein and inducing the expression of MK protein under the conditions of 20° C. and PH3 after proliferation at pH 4, said vector comprising a gene encoding a mature MK family protein ligated to a signal sequence of α1 factor from *Saccharomyces cerevisiae* and recovering secretory expression products.

9. The method according to claim 8, said method comprising:
   (a) culturing a transformant comprising methylotrophic yeast transformed with a vector for secretory expression of an intact MK family protein, said vector comprising a gene encoding a mature MK family protein ligated to a signal sequence of α1 factor from *Saccharomyces cerevisiae*, wherein said transformant is pPIC9DP-hMK/SMD1168, said MK family protein is MK protein, and said methylotrophic yeast is strain SMD1168,
   (b) inducing the expression of MK protein under the conditions of 20° C. and pH 3 after proliferation at pH 4, and
   (c) recovering secretory expression products.

10. The transformant, according to claim 5, wherein said vector comprises
   (a) a promoter sequence of a methanol-inducible alcohol oxidase gene (AOX1) from *Pichia pastoris*,
   (b) a signal sequence of α1 factor from *Saccharomyces cerevisiae*,
   (c) a gene encoding a mature MK family protein, wherein said gene is ligated to (b),
   (d) a transcription termination sequence of a methanol-inducible alcohol oxidase gene (AOX1) from *Pichia pastoris*,
   (e) a selection marker gene functioning in *Escherichia coli* and methylotrophic yeast,
   (f) a replication origin functioning in *Escherichia coli*, and
   (g) 5' and 3' end sequences of the AOX1 gene, wherein said sequences allow site-specific homologous recombination to a methylotrophic yeast chromosomal DNA to occur.

11. The transformant, according to claim 5, wherein said MK family protein is MK protein.

12. The transformant, according to claim 5, wherein said MK family protein is PTN protein.

13. The method, according to claim 8, wherein said transformant is pPIC9DP-hMK/SMD1168, said MK family protein is MK protein, and said methylotrophic yeast is strain SMD1168.

14. The method, according to claim 8, wherein said transformant is pPIC9-hPTN/GS115, MK family protein is PTN protein, and said methylotrophic yeast is strain GS115.

* * * * *

UNITED STATES PATENT AND TRADEMARK OFFICE
CERTIFICATE OF CORRECTION

PATENT NO.     : 6,867,037 B1
DATED          : March 15, 2005
INVENTOR(S)    : Akira Murasugi et al.

It is certified that error appears in the above-identified patent and that said Letters Patent is hereby corrected as shown below:

Title page,
Item [56], References Cited, OTHER PUBLICATIONS,
"Winther et al.," reference, "functions" should read -- function --.
"Rosenfeld et al.," "Recombinat" should read -- Recombinant --.

Column 1,
Line 45, "PV" should read -- PTN --.

Column 3,
Line 52, "sequencer" should read -- sequence --.
Line 55, "or" should read -- of --.
Line 61, "MF+1" should read -- MFα1 --.

Column 4,
Line 29, "αl factor" should read -- αl-factor --.
Line 35, "anal-factor" should read -- an α1-factor --.

Column 5,
Line 8, "M or F" should read -- MK or PTN --.

Column 6,
Line 1, "of in ethanol" should read -- of methanol --.
Line 3, "7-11189" should read -- 7-111891 --.
Line 18, "$A_{240}$" should read -- $A_{280}$ --.
Line 60, "G5115" should read -- GS115 --.
Line 66, "HE" should read -- MK --.

Column 8,
Line 39, "xpr ssion" should read -- expression --.

Column 9,
Lines 21, 24 and 58, "EcORI" should read -- EcoRI --.
Line 23, "EcORI, and inserted into the EcORI" should read -- EcoRI, and inserted into the EcoRI --.
Line 67, "war carried" should read -- was carried --.

UNITED STATES PATENT AND TRADEMARK OFFICE
CERTIFICATE OF CORRECTION

PATENT NO. : 6,867,037 B1
DATED : March 15, 2005
INVENTOR(S) : Akira Murasugi et al.

It is certified that error appears in the above-identified patent and that said Letters Patent is hereby corrected as shown below:

Column 10,
Line 34, "K" should read -- MK --.
Line 36, "pHILS51" should read -- pHILS1 --.
Line 40, "pHILS4" should read -- pHILD4 --.

Column 11
Line 10, "pPIC9X" should read -- pPIC9K --.
Line 11, "or" should read -- of --.
Line 45, "PM" should read -- MK --.
Line 57, "pPIC9" should read -- pPIC9K --.

Column 12,
Line 23, "Tyr-val" should read -- Tyr-Val --.
Line 25, "Tyr-val-Glu-Phe-Lys, 7 amino acids Tyr-val" should read
-- Tyr-Val-Glu-Phe-Lys, 7 amino acids Tyr-Val --.
Lines 26-27, "acids Tyr-val-Glu-Phe-Lys-Lys-Lys-Asp-Lys-val-" should read
-- acids Tyr-Val-Glu-Phe-Lys-Lys-Lys-Asp-Lys-Val- --.
Line 38, "ease" should read -- case --.

Column 13,
Line 31, "and aliquot" should read -- and an aliquot --.
Line 59, "acid, Cys" should read -- acid, and Cys --.
Line 61, "values of amino acid" should read -- values and values of amino acid --.

Column 14,
Line 53, "PT" should read -- PTN --.
Line 59, "EcORI" should read -- EcoRI --.
Line 66, "PA" should read -- PTN --.

Column 15,
Line 47, "2x sodium chloride" should read -- 2 M sodium chloride --.

Column 17,
Line 23, "(15303.9" should read -- (15303.8 --.

UNITED STATES PATENT AND TRADEMARK OFFICE
CERTIFICATE OF CORRECTION

PATENT NO. : 6,867,037 B1
DATED : March 15, 2005
INVENTOR(S) : Akira Murasugi et al.

Figure 17:
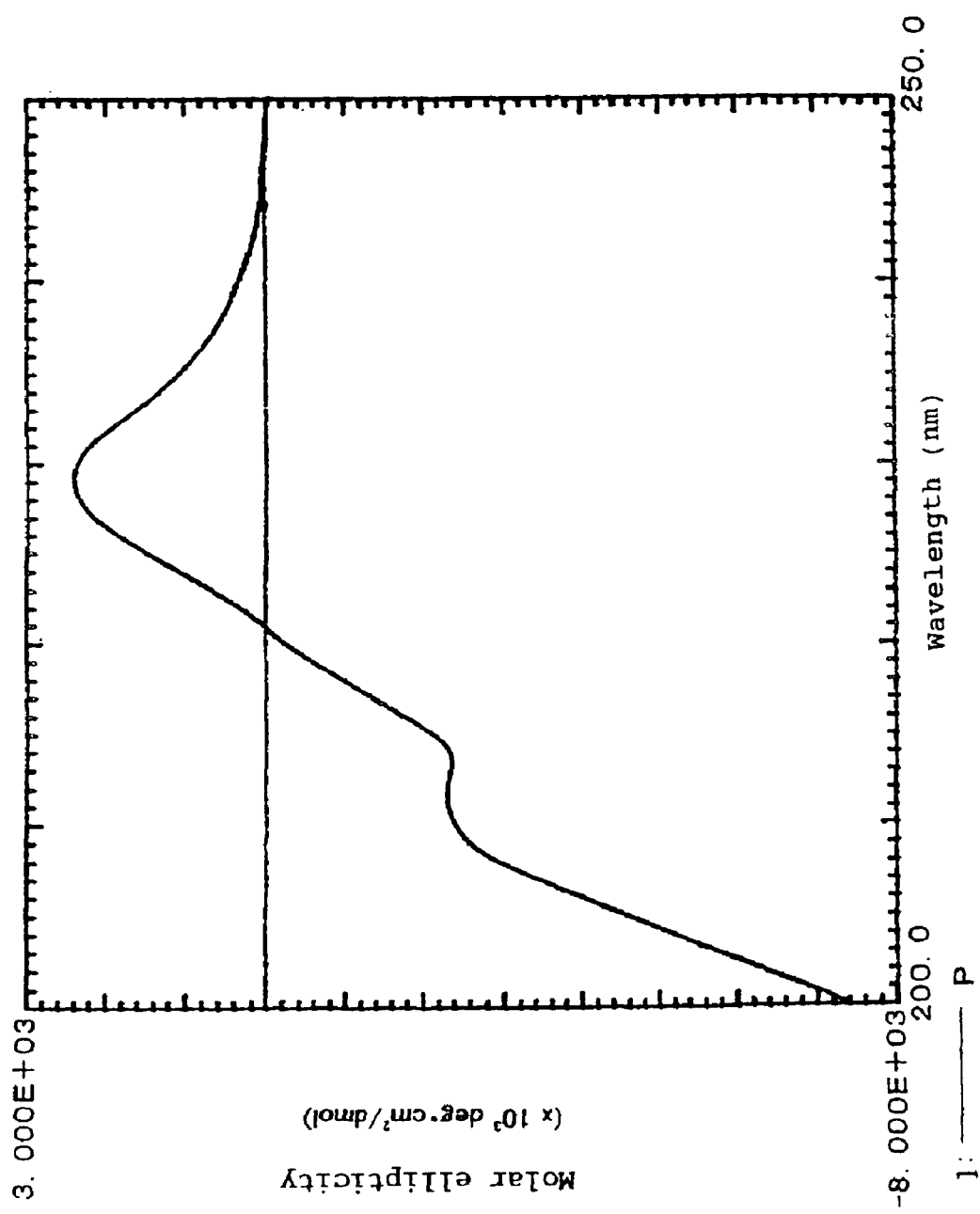
FIG. 17 shows a CD spectrum of human PTN purified from a fermentor culture supernatant of the expression strain pPIC9-hPTN/GS115. Ordinate (CD value) represents the molar ellipticity [θ(deg·cm²·decimol$^{-1}$)].

It is certified that error appears in the above-identified patent and that said Letters Patent is hereby corrected as shown below:

Column 18,
Line 7, "Fig. 11" should read -- Fig. 17 --.

Column 23,
Line 51, "at" should read -- $\alpha 1$ --.
Line 67, "PH3" should read -- pH3 --.

Column 24,
Line 64, ", MK" should read -- , said MK --.

Signed and Sealed this

Sixth Day of September, 2005

JON W. DUDAS
*Director of the United States Patent and Trademark Office*